US007482128B2

(12) United States Patent
Jensen et al.

(10) Patent No.: US 7,482,128 B2
(45) Date of Patent: Jan. 27, 2009

(54) ANTI-FELINE ALBUMIN ANTIBODIES

(75) Inventors: Wayne A. Jensen, Wellington, CO (US); Shirley Wu Hunter, Fort Collins, CO (US); Karen Sverlow, Dixon, CA (US); Janet S. Andrews, Westminster, CO (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 10/550,563

(22) PCT Filed: Mar. 25, 2004

(86) PCT No.: PCT/US2004/009135

§ 371 (c)(1),
(2), (4) Date: Aug. 14, 2006

(87) PCT Pub. No.: WO2004/084841

PCT Pub. Date: Oct. 7, 2004

(65) Prior Publication Data

US 2006/0281131 A1 Dec. 14, 2006

(51) Int. Cl.
*G01N 33/53* (2006.01)

(52) U.S. Cl. ........................ 435/7.1; 435/7.2; 435/7.91; 435/7.92; 436/516; 436/518

(58) Field of Classification Search .................. 435/7.1, 435/7.2, 7.91, 7.92; 436/516, 518
See application file for complete search history.

(56) References Cited

U.S. PATENT DOCUMENTS 4,163,778 A * 8/1979 Ohman et al. .............. 24/276.1
4,281,061 A 7/1981 Zuk et al.
4,659,678 A * 4/1987 Forrest et al. ............... 436/512
4,804,625 A 2/1989 Morrison et al.
5,073,484 A 12/1991 Swanson et al.
5,087,575 A 2/1992 Lau
5,246,835 A 9/1993 Suzuki et al.
5,403,744 A 4/1995 Zimmerle
5,415,994 A 5/1995 Imrich et al.
5,424,193 A 6/1995 Pronovost et al.
5,656,502 A 8/1997 MacKay et al.
6,001,658 A 12/1999 Fredrickson
6,153,392 A 11/2000 Liao et al.
6,190,878 B1 2/2001 Pierson et al.
7,172,873 B2 * 2/2007 McDonald et al. ........... 435/7.1
2002/0187133 A1 * 12/2002 Kubota et al. ............ 424/93.21
2004/0175754 A1 * 9/2004 Bar-Or et al. ................ 435/7.1

FOREIGN PATENT DOCUMENTS

EP 0 198 639 A1 10/1986
EP 0830206 1/2001
JP 404249941 A 9/1992
JP 5-302922 11/1993
WO WO 94/01775 1/1994
WO WO 94/29696 12/1994
WO WO 96/40434 12/1996
WO WO 00/37944 6/2000

OTHER PUBLICATIONS

Bakris, George L., *Curr. Opin. in Neph. and Hypertension*, 1996, vol. 5, pp. 219-223.
Bakris, G.L., *J. Clin. Hypertens* (*Greenwich*), 2001, vol. 2, pp. 99-102.
Batamuzi, et al., *Veterinary Record*, 1998, vol. 143, pp. 16-20.
Berrut, et al., *Clinical Nephrology*, 1997, vol. 48, No. 2, pp. 92-97.
German, et al., *Veterinary Immunology and Immunopathology*, 1998, vol. 64, pp. 107-121.
Kilaru, et al., *Journal of Human Hypertension*, 1994, vol. 8, pp. 809-817.
Mogensen, C.E., *Diabetologia*, 1999, vol. 42, pp. 263-285.
Pinto-Sietsma, et al., *J Am Soc Nephrol*, 2000, vol. 11, pp. 1882-1888.
Vaden, *Proc. 17th ACVIM*, 1999, 420.
Viberti, GianCarlo, *American Journal of Hypertension, Ltd*., 1994, vol. 7, pp.
Watts, *Clin. Chem*.,, 1986, vol. 32, No. 8, pp. 1544-1548.
Syme, et al., Proceedings 18th ACVIM, Seattle, WA, May 25-28, 2000, Abstract #97.
Burne, et al., 1998, *Clinical Science*, vol. 95, pp. 67-72.
Comper, et al., Feb. 2003, *American Journal of Kidney Diseases*, vol. 41, No. 2, pp. 336-342.
Osicka, et al., Sep. 2000, *Diabetes*, vol. 49, pp. 1579-1584.
Miller, et al., 1993, *Electrophoresis*, vol. 14, pp. 1312-1317.
Pandjaitan, et cl., 2000, *J. Allergy Clin. Immunol.*, vol. 105 (2 Pt 1), pp. 279-285.
Hilger, et al., 1996, *Gene*, vol. 169, pp. 295-296.
Ho, et al., 1993, *Eur. J. Biochem*., vol. 215, pp. 205-212.

* cited by examiner

*Primary Examiner*—Mark L Shibuya
*Assistant Examiner*—Jacob Cheu

(57) ABSTRACT

The present invention provides isolated monoclonal antibodies that selectively bind albumin from animals. Also provided are methods using such antibodies for the detection of early renal disease in animals. The method includes the steps of (a) obtaining a sample from an animal to be tested; (b) contacting the sample with an antibody having a greater avidity for feline albumin than for other proteins or components in the sample; (c) detecting the complex formed by the antibody and albumin; and (d) determining the amount of albumin in the sample from the amount of antibody-albumin complex detected. An amount of albumin in the range of from 10 μg/ml to about 300 μg/ml indicates the presence of early renal disease.

2 Claims, No Drawings

ANTI-FELINE ALBUMIN ANTIBODIES

CROSS-REFERENCE TO RELATED APPLICATIONS

This application claims priority to international PCT Application No. PCT/US2004/009135, filed Mar. 25, 2004; which claims priority to U.S. patent application Ser. No. 10/444,940, filed May 22, 2003, entitled "NOVEL ANTI-FELINE ALBUMIN ANTIBODIES AND METHODS OF DETECTING EARLY RENAL DISEASE"; which claims priority to U.S. patent application Ser. No. 10/431,155, filed May 7, 2003, entitled "METHODS OF DETECTING EARLY RENAL DISEASE IN ANIMALS"; which claims priority to U.S. patent application Ser. No. 10/401,936, filed Mar. 27, 2003, entitled "METHODS FOR DETECTING EARLY RENAL DISEASE IN ANIMALS"; and all of the foregoing incorporated by reference herein.

FIELD OF THE INVENTION

The present invention relates to detection of early renal disease in animals, and more particularly to use of microalbuminuria as a marker of early renal disease.

BACKGROUND OF THE INVENTION

Glomerular disease is a broad term used to describe a number of renal diseases that can lead to renal failure and death. Damage to the glomerulus increases capillary permeability to proteins such as albumin, resulting in the presence of proteins in urine (referred to as proteinuria).

In humans, proteinuria can result from a number of diseases, including diabetes, hypertension and IgA nephropathy. The conventional test for proteinuria in humans is to use a standard protein dipstick assay as described, for example, in Bakris, *Curr. Opin. in Neph. and Hypertension,* 5:219-223 (1996). Dipsticks that are chemically impregnated with sulfosalicylic acid to measure proteins in a sample are commercially available, for example from Boehringer-Mannheim, Germany (Chemstrips™) and Ames Co., USA (Albustix™). One drawback to these dipstick assays is that they require a significant amount of protein in the urine to be detected. Amounts of protein in humans of less than 300 milligrams per day are not detectable by the dipstick assay, yet proteinuria may still be present. Another drawback to these protein-based assays is that they are incapable of discriminating between different types of protein (e.g., albumin, globulin, etc.) that may be present in urine. Proteinuria may result from the leakage of serum proteins into glomerular filtrate due to glomerulenephritis or to dysfunction of the renal tubular reabsorption system; however, proteinuria may also be present due to problems unrelated to renal disease such as bladder infections or a high-protein diet.

Lower amounts of albumin in the urine, referred to as "microalbuminuria," indicate a level of albumin that is greater than in normal patients, but lower than in patients with overt proteinuria, i.e., clinically proteinuric. In humans, microalbuminuria refers to amounts of albumin between 30 milligrams per day and 300 milligrams per day according to Watts, *Clin. Chem.,* 32(8):1544-1548 (1986). Methods to detect human microalbuminuria are known and include those methods that use an anti-human albumin antibody to detect amounts of human albumin that are not detectable by known dipstick methods. Such methods of detecting human microalbuminuria are described, for example, in U.S. Pat. No. 5,246,835, issued on Sep. 21, 1993, to Suzuki et al.

Although microalbuminuria can be detected in humans, the utility of detecting microalbuminuria in humans may be very limited, at least according to some reports. For example, using the microalbuminuria tests to predict renal disease has only been recommended for humans with diabetes according to Bakris, supra. Because disorders other than diabetes, such as hypertension, heart disease and IgA nephropathy do not lead to consistent microalbuminuria in humans, according to Bakris, supra, detecting microalbuminuria has poor predictive value for later renal disease associated with these non-diabetic disorders states. Accordingly, using microalbuminuria tests to screen for potential or early renal disease in non-diabetic human patients is generally not recommended by Bakris, supra.

Renal disease is also a significant health problem in companion animals, particularly dogs and cats. In dogs, the primary cause of renal disease is damage to the glomerulus in the kidney. Although glomerular damage in dogs can occur in any number of ways, it is most commonly caused when circulating immune complexes (i.e., antibody/antigen complexes) are deposited in the glomerular capillaries as a result of systemic illness as described in Batamuzi, et al., *Vet Record,* 143;16-20 (1988). Several diseases have been implicated in the pathogenesis of immune complex formation, including for example, dirofilariasis and other parasitic infections, diabetes, hypothyroidism and others.

Glomerular dysfunction may also be present in cats suffering from renal disease. Alternatively, the initial renal damage in cats may be tubular and/or interstitial in nature. For example, renal disease in cats may result from a dysfunction of the reabsorption process in the tubules. This latter form of renal damage may result in microalbuminuria long before there is any obvious damage to the glomerulus.

Early renal disease in veterinary medicine has typically been characterized by glomerular changes detectable by histopathology, including the use of light microscopy or occasionally immunofluorescence as reported in Vaden, *Proc. 17th ACVIM,* 420 (1999). However, as reported in that paper, these techniques can lead to misdiagnosis of the cause of the renal disease. Determining the cause of the renal disease is useful in formulating an appropriate treatment regimen. For example, if the cause of the renal disease is immune-mediated, then immunosuppressive therapy may be appropriate. However, currently available assays to detect human microalbuminuria are not sufficiently sensitive to detect microalbuminuria in animals.

SUMMARY OF THE INVENTION

The present invention relates to novel monoclonal antibodies that selectively bind albumin from a felid (also referred to as "feline albumin"). Such monoclonal antibodies include, for example, H419, H420, H421, H422, H423, H424, H425, H426, H427, H428, H429, H430, H431, H432, H433, H434, H435, H436, H438, H439, H440, H441, H442, H443, H446, H447, H448, H449, H451, H452, H454, H455, H456, H457, H458, H459 and H460. Useful monoclonal antibodies of the present invention can have a greater avidity for feline albumin than for albumin of other species.

The monoclonal antibodies of the present invention are capable of inhibiting the binding of an albumin-binding compound to feline albumin. Alternatively or in addition, the monoclonal antibodies can bind to the same epitope of feline albumin recognized by an albumin-binding compound. An albumin-binding compound can be an antibody such as, for example, TNB1, TNB4, TNB5, TNB6, H352, H386, H387, H388, H389, H390, H391, H393, H394, H395, H396, H397, H398, H399, H400, H401, H402, H419, H421, H422, H423, H424, H425, H426, H427, H428, H429, H430, H431, H432, H434, H435, H436, H437 H438, H439, H440, H441, H442, H443, H446, H447, H449, H451, H452, H453, H454, H455, H456, H457, H458, H459 or H460.

The present invention also includes novel cell lines that produce the novel monoclonal antibodies of the present invention.

The present invention further relates to methods of using antibodies having a greater avidity for feline albumin than for other proteins or components in a sample to detect early renal disease in felids. Such antibodies include the novel monoclonal antibodies of the present invention as well as other antibodies as disclosed more fully herein. The methods of the present invention are based on the discovery that the presence of feline albumin in a sample in the range of about 10 μg/ml to about 300 μg/ml, when the specific gravity of the sample is normalized to 1.010, is indicative of early renal disease. Thus, the methods are generally accomplished by:

(a) obtaining a sample from an animal;

(b) contacting the sample with an antibody that has a greater avidity for feline albumin than for other proteins or components in the sample;

(c) detecting the complex formed by the antibody and albumin; and (d) determining the amount of albumin present in the sample from the amount of antibody-albumin complex detected.

If the amount of albumin present in the sample falls within the range of about 10 μg/ml to about 300 μg/ml, when the specific gravity of the sample is normalized to 1.010, then early renal disease is indicated for the animal. Urine can be used in the methods as the sample, although any sample that is useful for measuring leakage of albumin from the glomerulus or dysfunction of the renal tubular reabsorption process can be used. The amount of albumin in the sample can be assayed by any method capable of detecting albumin, including, for example, immunologically-based assays. Examples of useful assays include single step assays, dipstick-based assays and ELISAs.

Kits containing the novel antibodies of the present invention and means for detecting the amount of albumin in a sample are also provided. Such kits are useful for performing the methods of the present invention.

DETAILED DESCRIPTION OF THE INVENTION

The present invention generally relates to a novel method of detecting early renal disease in animals and to novel monoclonal antibodies that selectively bind to albumin from a felid. More particularly, the present invention relates to the discovery that the disclosed antibodies and methods can be used to predict early renal disease in animals as they can be used to detect microalbuminuria. Therefore, the methods can also be useful for prescribing a treatment for an animal. Suitable treatment can be designed to delay or prevent the onset of late-stage renal disease. Examples of such treatment include, for example, pharmacological or dietary modification. The present invention is also useful in monitoring the effectiveness of a prescribed treatment.

A method of the present invention can be generally accomplished by:

(a) obtaining a sample from an animal;

(b) contacting the sample with an antibody that has a greater avidity for feline albumin than for other proteins or components present in the sample;

(c) detecting the complex formed by the antibody and the albumin; and (d) determining the amount of albumin present in the sample from the amount of antibody-albumin complex detected. An amount of albumin in a range of from about 10 μg/ml to about 300 μg/ml in the sample is indicative of early renal disease.

It is to be noted that the term "a" entity or "an" entity refers to one or more of that entity. For example, a protein refers to one or more proteins or at least one protein. As such, the terms "a" "an" "one or more" and "at least one" can be used interchangeably herein. The terms "comprising," "including," and "having" can also be used interchangeably. In addition, the terms "amount" and "level" are also interchangeable and may be used to describe a concentration or a specific quantity. Furthermore, the term "selected from the group consisting of" refers to one or more members of the group in the list that follows, including mixtures (i.e. combinations) of two or more members.

As used herein, the terms "renal disease" and "renal damage" are defined as a dysfunction of the glomerular filtration process or a dysfunction of the tubular reabsorption process. As such, the terms "renal disease" and "renal damage" can be used interchangeably herein. Kidney dysfunction may be transient or it may be chronic, depending on the underlying cause of the disease. One consequence of renal disease is that proteins which are normally retained in the blood, leak through the glomerulus, into the glomerular filtrate and eventually into the urine. In some cases, the tubular reabsorption process fails resulting in proteins that are normally reabsorbed being released into the urine. One example of a protein which may be present in urine due to glomerular or tubular reabsorption dysfunction is albumin and its presence in urine at low levels has been termed microalbuminuria. The term "microalbuminuria," as used herein, refers to an amount of albumin that is present in a sample in a range from about 10 μg/ml to about 300 μg/ml when the sample is normalized to a specific gravity of 1.010. This is greater than the amount found in healthy animals which is typically low, i.e., less than 10 μg/ml. Microalbuminuria may arise as a consequence of damage to the kidney resulting from, for example, immune-complex-mediated glomerulernephritis. It may also result, for example, as a consequence of the failure of the tubular reabsorption mechanism. As used herein, the term "late-stage renal disease" is used to define a state in which an animal has lost 70% or more of its renal function, with corresponding, elevated levels in the animal's serum metabolites, in particular blood-urea nitrogen (BUN) and serum creatinine levels. As used herein, the term "early renal disease" is defined as the presence of microalbuminuria in an animal in the absence of detectable changes in renal function (i.e. increased BUN, serum creatinine or decreased ability to concentrate urine). As such, an albumin level in a sample ranging from about 10 μg/ml to about 300 μg/ml when the sample is normalized to a specific gravity of 1.010 is indicative of early renal disease.

As used herein, the term "animal" is meant to encompass any non-human organism capable of developing early renal disease. Suitable animals to test for microalbuminuria include, but are not limited to companion animals (i.e. pets), food animals, work animals, or zoo animals. Preferred animals include, but are not limited to, cats, dogs, horses, ferrets and other Mustelids, cattle, sheep, swine, and rodents. More preferred animals include cats, dogs, horses and other companion animals, with cats, dogs and horses being even more preferred. As used herein, the term "companion animal" refers to any animal which a human regards as a pet. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat is a domestic cat. As used herein, a dog refers to any member of the family Canidae, including, but not limited to, domestic dogs, wild dogs, foxes, wolves, jackals, and coyotes and other members of the family Canidae. A preferred dog is a domestic dog. As used herein, a horse refers to any member of the family Equidae. An equid is a hoofed mammal and includes, but is not limited to, domestic horses and wild horses, such as, horses, asses, donkeys, and zebras. Preferred horses include domestic horses, including race horses.

In one embodiment of the present invention, a sample is obtained, or collected, from an animal to be tested for microalbuminuria. The animal may or may not be suspected of having early stage renal disease. A sample is any specimen obtained from the animal that can be used to measure albumin leakage from the glomerulus. A preferred sample is a bodily fluid that can be used to measure albumin leakage from the glomerulus or dysfunction of the renal tubular reabsorption process. Those skilled in the art can readily identify appropriate samples.

Urine is particularly suitable as the sample. Urine samples can be collected from animals by methods known in the art, including, for example, collecting while the animal is voiding, or collecting by catheterization, or by cystocentesis. Urine may be refrigerated or frozen before assay, but is preferably assayed soon after collection.

Although not necessary for the present invention, the sample may be pre-treated as desired. For example, the sample can be normalized to a desired specific gravity. Normalizing the sample by appropriate dilution methods known in the art permits quantification of microalbuminuria independent of the original concentration (e.g. specific gravity) of the sample. Although any desired specific gravity can be readily selected by those skilled in the art, a particularly suitable specific gravity is 1.010. If another specific gravity value is desired for normalizing a sample, those skilled in the art can readily determine the appropriate albumin amounts that would fall within the definition of microalbuminuria for the desired specific gravity.

After obtaining the sample, the level of albumin in that sample is determined. As used herein, the terms "determine," "determine the level of albumin," "determine the amount of albumin," "determine the albumin level," and the like are meant to encompass any technique which can be used to detect or measure the presence of albumin in a sample. Albumin is an example of an analyte. The term "analyte", as used herein, is used to describe any molecule or compound present in a sample. Such techniques may give qualitative or quantitative results. Albumin levels can be determined by detecting the entire albumin protein or by detecting fragments, degradation products or reaction products of albumin.

In the methods of the present invention, the level of albumin is determined using the novel anti-feline albumin monoclonal antibodies described herein and other suitable albumin-binding compounds. As used herein, the terms "albumin-binding molecule," "albumin-binding compound," "anti-albumin compound," and the like are used interchangeably and refer to any molecule which binds to albumin and forms a stable complex. A stable complex is one in which the binding partners associate for a period of time long enough to allow detection of the complex using the methods described herein. Particularly useful albumin-binding compounds are those that selectively bind albumin from an animal. The term "selectively bind albumin" refers to the ability of a compound to preferentially bind albumin as opposed to binding proteins unrelated to albumin or non-protein components present in the sample. A compound that preferentially binds albumin is one that binds albumin but does not significantly bind other molecules or components that may be present in the sample. Significant binding is considered, for example, binding of an albumin-binding compound to a non-albumin molecule with an affinity or avidity great enough to interfere with the ability of the albumin-binding compound to determine the level of albumin in a sample. Examples of such other molecules and components that may be present in a sample include, but are not limited to, non-albumin proteins, lipids and carbohydrates. Examples of non-albumin proteins include, but are not limited to, hemoglobin, collagen, lysozyme, aquaporin-2 and fibrinogen.

One embodiment of the present invention is an albumin-binding compound that selectively binds albumin from a felid, i.e. feline albumin-binding compound. Such a compound does not react with non-albumin components in a sample, but can show avidity, affinity or selective binding for albumin from other species. Such reactivity is also referred to as cross reactivity as the feline albumin-binding compound reacts with albumin from another animal specie. Such an avidity or affinity is typically less than the avidity or affinity of the albumin-binding compound for feline albumin.

For example, a feline-albumin-binding compound of the present invention can, but need not, bind feline albumin with an avidity or affinity more than about 2 times (i.e., 2×), more than about 3×, more than about 4×, more than about 5×, more than about 6×, more than about 7×, more than about 8×, more than about 9× or more than about 10× greater than the compound's avidity or affinity for albumin from other species. Such avidities or cross-reactivities can be determined by those skilled in the art and methods to do so include, but are not limited to ELISA assays, equilibrium dialysis and Scatchard analysis. The degree of cross reactivity possessed by an albumin-binding compound may be represented as indicated above (e.g. 2×) or, for example, as a ratio or a percentage. Terms used to represent cross-reactivity values are understood by and known to those skilled in the art.

A particularly useful albumin-binding compound of the present invention is an antibody that selectively binds albumin from a feline. As used herein, the terms "anti-feline albumin antibody," "antibody to feline albumin," "antibody having specificity for feline albumin," "animal albumin antibody," and the like refer to an antibody that selectively binds albumin from a felid. Suitable anti-feline albumin antibodies preferentially bind to feline albumin but may also bind to albumin from other species. Such antibodies, though, do not significantly bind to non-albumin related components. As such, an anti-albumin antibody of the present invention preferentially binds to feline albumin as opposed to binding to feline proteins unrelated to albumin. The present invention also includes isolated (i.e,, removed from their natural milieu) antibodies that selectively bind to feline albumin. Isolated antibodies of the present invention can include antibodies in serum or other medium, e.g. blood, ascites or any other fluid, or antibodies that have been purified to varying degrees. Antibodies useful in the methods of the present invention can be polyclonal or monoclonal, or can be functional equivalents such as antibody fragments and genetically-engineered antibodies, including single chain antibodies or chimeric antibodies that can bind to one or more epitopes on albumin.

Antibodies of the present invention have binding affinities for albumin, for example, of greater than about $1\times10^6$, of greater than about $1\times10^7$, of greater than about $1\times10^8$, of greater than about $1\times10^9$, of greater than about $1\times10^{10}$, of greater than about $1\times10^{11}$, of greater than about $1\times10^{12}$ liters/mol. Methods of determining binding affinities and avidities are well known to those skilled in the art and are also described in detail in Janeway et al., *Immunobiology: The Immune System in Health and Disease* (Garland Publishing Company, 1996).

Suitable antibodies of the present invention are those having the characteristic of being able to bind feline or canine albumin when the albumin is at a concentration of between about 10 μg/ml and about 300 μg/ml. Particularly useful antibodies bind feline albumin when the albumin is at a concentration of about 10 μg/ml, about 25 μg/ml or less, about 50 μg/ml or less, about 75 μg/ml or less, about 100 μg/ml or less, about 125 μg/ml or less, about 150 μg/ml or less, about 175 μg/ml or less, about 200 μg/ml or less, about 250 μg/ml or less, or less than about 300 μg/ml.

Particularly suitable antibodies are those that detect albumin when the amount of albumin in the sample is about 50 μg/ml or less, more preferably about 25 μg/ml or less, more preferably about 10 μg/ml and the detection method is a dipstick device described in U.S. Pat. No. 6,001,658. Such antibodies are described in the accompanying Examples.

A suitable antibody of the present invention is one which competes with any of the monoclonal antibodies TNB1, TNB4, TNB5, TNB6, H352, H386, H387, H388, H389, H390, H391, H393, H394, H395, H396, H397, H398, H399, H400, H401, H419, H420, H421, H422, H423, H424, H425, H426, H427, H428, H429, H430, H432, H433, H434, H435, H436, H437 H438, H439, H440, H441, H442, H443, H447, H448, H449, H451, H452, H453, H454, H455, H456, H457, H458, H459 for binding to feline albumin. As used herein, the terms "compete" and "inhibit selective binding" refer to the ability of an antibody to prevent another antibody or other anti-albumin compound from binding to the same albumin.

Antibodies useful for practicing the present invention may bind to one or more regions or domains of albumin. Such antibodies may recognize epitopes comprising solvent-accessible residues, epitopes comprising buried residues or epitopes comprising both solvent accessible residues and buried residues. Solvent accessible residues are residues that would be expected to be or have been shown to be on the outer surface of the native protein, and therefore accessible to the solvent containing the protein. Buried residues are residues that would be expected to be or have been shown to be in the interior of the native molecule, and are inaccessible to the solvent containing the protein. Such buried residues may become exposed if the protein changes conformation or becomes denatured. One embodiment of the present invention is an antibody that binds to the same or related epitope bound by the antibodies TNB1, TNB4, TNB5, TNB6, H352, H386, H387, H388, H389, H390, H391, H393, H394, H395, H396, H397, H399, H400, H401, H402, H419, H420, H421, H422, H423, H424, H425, H426, H428, H429, H430, H431, H432, H433, H434, H435, H436, H437 H438, H439, H441, H442, H443, H446, H447, H448, H449, H451, H452, H453, H454, H455, H457, H458, H459 and H460.

It is widely known in the art that albumin is comprised of various domains and sub-domains, as described, for example, in Ruker, *Journal of Biological Chemistry,* V.274, No. 41:29303-29310 (1999). In one embodiment, useful antibodies of the present invention bind an epitope within a domain selected from domain I, domain II or domain III. In a particular embodiment, antibodies of the present invention bind an epitope within a sub-domain selected from sub-domain IA, sub-domain IB, sub-domain IIA, sub-domain IIB, sub-domain IIIA or sub-domain IIIB. One embodiment of the present invention is an antibody that binds an epitope within Sudlow's sites I or II. In a particular embodiment, antibodies of the present invention bind an epitope that is present in a region selected from a region defined by amino acids 1-197, a region defined by amino acids 189-385, a region defined by amino acids 381-585, a region defined by amino acids 199-292 and a region defined by amino acids 384-489. In one embodiment, antibodies of the present invention bind an epitope that is present in a region selected from a region defined by amino acids 1-50, a region defined by amino acids 51-100, a region defined by amino acids 101-150, a region defined by amino acids 151-200, a region defined by amino acids 201-250, a region defined by amino acids 251-300, a region defined by 301-350, a region defined by amino acids 351-400, a region defined by amino acids 401-450, a region defined by amino acids 451-500, a region defined by amino acids 501-550, and a region defined by amino acids 551-600. Additionally useful antibodies of the present invention are those that bind an epitope that is present in a region selected from a region defined by amino acids 1-25, a region defined by amino acids 26-75, a region defined by amino acids 76-125, a region defined by amino acids 126-175, a region defined by amino acids 176-225, a region defined by amino acids 226-275, a region defined by 276-325, a region defined by amino acids 326-475, a region defined by amino acids 476-525, a region defined by amino acids 526-575, and a region defined by amino acids 576-600.

A suitable method to produce antibodies effective for use in the present invention includes (a) administering to an animal an effective amount of a protein, peptide or mimetope thereof to produce the antibodies and (b) recovering the antibodies. Antibodies raised against defined proteins or mimetopes can be advantageous because such antibodies are not substantially contaminated with antibodies against other substances that might otherwise cause interference in a diagnostic assay. Methods to produce such antibodies are known in the art and are described in detail in Harlow et al., *Antibodies, a Laboratory Manual* (Cold Spring Harbor Labs Press, 1988), and include immunizing animals to produce preparations of antibodies that are recovered from, for example, serum or ascites fluid and purified by methods known in the art to yield preparations that are reactive to animal albumin. Many species have proteins sharing closely related sequences and therefore it may be difficult using standard immunization protocols to produce antibodies which recognize a protein from only one specie. Therefore, modification of standard methods used to produce antibodies, such as, for example, subtractive hybridization techniques, are also contemplated. Such modifications can be those known to those skilled in the art or as disclosed herein. In another method, antibodies for use in the present invention are produced recombinantly using techniques disclosed in Sambrook et al., *Molecular Cloning: A Laboratory Manual,* (Cold Spring Harbor Labs Press, 1989).

The present invention includes monoclonal antibodies and methods to produce such antibodies. Briefly, monoclonal antibodies are produced from the fusion of spleen cells from an immunized animal and myeloma cells to produce a hybridoma. Hybridomas can be screened for production of the proper antibody, then cultured and the antibodies harvested. As used herein, the term "cultured cell" refers to hybridomas or any other cell line that produces an antibody. Methods to produce and screen such cultured cells are described in Harlow, et al., supra. While there are existing methods to prepare an antigen so that antibodies produced will be reactive with animal albumin, see for example, Harlow, et al., supra, the present invention includes the discovery of a method to efficiently produce anti-feline monoclonal antibodies. Such procedures are described in Examples 17 and 18. Preparation of the antigen material for injection into the animal includes any technique known in the art, and include, for example, using the full-length protein, using peptides selected from immunogenic regions of the protein, modifying the antigen by methods such as, for example, dinitrophenol coupling, arsynyl coupling, denaturation of the antigen, coupling antigen to protein carriers such as, for example, keyhole limpet hemacyanin, peptides containing Class II- T-cell receptor binding sites, to beads, and any other method known in the art. See Harlow, et al., supra.

The anti-albumin antibodies useful in the methods of the present invention can include multifunctional antibodies, for example a bifunctional antibody having at least one functional portion that specifically binds to albumin. Such multifunctional antibodies can include, for example, a chimeric molecule comprising a portion of the molecule that binds to albumin and a second portion that enables the chimeric molecule to be bound to a substrate or to be detected in such a manner that the binding to the albumin is unimpaired. Examples of suitable second portions include but are not limited to a fragment of an immunoglobulin molecule, a fluorescent protein or an enzyme.

Hybrids or fusions of albumin-binding proteins which retain their albumin-binding ability may also be used. In such hybrids, the albumin-binding portion of the protein would be joined to a second portion which allows the hybrid to be bound to a substrate or to be detected. Examples of suitable second portions include, but are not limited to, a fragment of an immunoglobulin molecule, an epitope tag, a fluorescent protein or an enzyme.

An albumin-binding molecule used in the present invention can be contained in a formulation. For example, an antibody can be combined with a buffer in which the antibody is solubilized, and/or with a carrier. Suitable buffers and carriers are known to those skilled in the art. Examples of suitable buffers include any buffer in which an albumin-binding molecule can function to selectively bind to albumin, such as, but not limited to, phosphate buffered saline, water, saline, phosphate buffer, HEPES buffer (N-2-hydroxyethylpiperazine-N'-2-ethansulfonic acid buffered saline) TES buffer (Tris—EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be combined with an albumin-binding molecule or conjugated (i.e. attached) to an albumin-binding molecule in such a manner as to not substantially interfere with the ability of the albumin-binding molecule to selectively bind to albumin. In addition, suitable formulations of the present invention can include not only the albumin-binding molecule to specie-specific albumin, but also one or more additional antigens or antibodies useful for detecting albumin.

As used herein, the term "contacting" refers to the introduction of a sample putatively containing albumin to an albumin-binding compound, for example, by combining or mixing the sample with the albumin-binding compound. When albumin is present in the sample, an albumin-compound complex is then formed; such complex formation refers to the ability of an anti-albumin compound to selectively bind to the albumin in order to form a stable complex that can be detected. Detection can be qualitative, quantitative, or semi-quantitative. Binding albumin in the sample to the albumin-binding compound is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, enzyme immunoassays (e.g., ELISA), immunoprecipitations, immunoblot assays and other immunoassays as described, for example, in Sambrook et al., supra, and Harlow, et al., supra. These references also provide examples of complex formation conditions.

In one embodiment, an albumin/albumin-binding compound complex, also referred to herein as an albumin-compound complex, can be formed in solution. In another embodiment, an albumin/albumin-binding compound complex can be formed in which the albumin or the albumin-binding compound is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a sponge, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) *A Practical Guide to ELISA,* Pergamon Press, Elmsford, N.Y. pp 33-44, and Price, C. and Newman, D. eds. *Principles and Practice of Immunoassay,* $2^{nd}$ edition (1997) Stockton Press, NY, N.Y.

An anti-albumin compound can be immobilized on a substrate, such as a microtiter dish well, a dipstick, an immunodot strip, or a lateral flow apparatus. A sample collected from an animal is applied to the substrate and incubated under conditions suitable (i.e., sufficient) to allow for anti-albumin compound-albumin complex formation bound to the substrate (i.e., albumin in the sample binds to the anti-albumin compound immobilized on the substrate).

In accordance with the present invention, once formed, an albumin-binding compound/albumin complex is detected. As used herein, the term "detecting complex formation" refers to identifying the presence of albumin-binding compound complexed to albumin. If complexes are formed, the amount of complexes formed can, but need not be, quantified. Complex formation, or selective binding, between a putative albumin-composition with an albumin-binding compound can be measured (i.e., detected, determined) using a variety of methods standard in the art (see, for example, Sambrook et al. supra.), examples of which are disclosed herein. A complex can be detected in a variety of ways including, but not limited to use of one or more of the following assays: an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BioCore™ assay (e.g., using colloidal gold), an immunodot assay (e.g., Heska AG's Immunodot System, Fribourg, Switzerland), and an immunoblot assay (e.g., a western blot), a phosphorescence assay, a flow-through assay, a chromatography assay, a polyacrylamide gel (PAGe)-based assay, a surface plasmon resonance assay, a spectrophotometric assay, a particulate-based assay, and an electronic sensory assay. Such assays are well known to those skilled in the art.

Assays can be used to give qualitative or quantitative results depending on how they are used. The assay results can be based on detecting the entire albumin molecule or fragments, degradation products or reaction products of albumin. Some assays, such as agglutination, particulate separation, and immunoprecipitation, can be observed visually (e.g., either by eye or by a machines, such as a densitometer or spectrophotometer) without the need for a detectable marker.

In other assays, conjugation (i.e., attachment) of a detectable marker to the anti-albumin compound or to a reagent that selectively binds to the anti-albumin compound (e.g., an antibody to an anti-albumin antibody) aids in detecting complex formation. Such compounds and reagents are examples of detection molecules (i.e. molecules that enable the detection of albumin). A detectable marker can be conjugated to the detection molecule at a site that does not interfere with the ability of the detection molecule to enable the detection of albumin. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A bead refers to a particulate substrate composed of a matrix such as latex or polystyrene, which can be covalently or non-covalently cross-linked to a detection molecule. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure® NeutrAvidin). For example, in a preferred embodiment, an anti-albumin antibody is conjugated to a latex bead.

The present invention can further comprise one or more layers and/or types of secondary molecules or other binding molecules capable of detecting the presence of an albumin-binding compound/albumin complex. For example, an untagged (i.e., not conjugated to a detectable marker) secondary antibody that selectively binds to an albumin-binding compound, can be bound to a tagged (i.e., conjugated to a detectable marker) tertiary antibody that selectively binds to the secondary antibody to enable detection of albumin. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

One embodiment to detect microalbuminuria involves the use of a lateral flow assay, examples of which are described in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al. A lateral flow assay is an example of a single-step assay. In a single-step assay, once the sample has been obtained and made ready for testing, only a single action is necessary on the part of the user to detect the present of an analyte. For example, the sample, in whole or part, can be applied to a device which then measures analyte in the sample. In one embodiment, a sample is placed in a lateral flow apparatus that includes the following components: (a) a support structure defining a flow path; (b) a labeling reagent comprising a bead conjugated to a specific antibody, the labeling reagent being impregnated within the support structure in a labeling zone; and (c) a capture reagent. Preferred antibodies include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose, PVDF, or carboxymethylcellulose. The support structure defines a flow path that is lateral and is divided into zones, namely a labeling zone and a capture zone. The apparatus can further include a sample receiving zone located along the flow path, preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In another embodiment, a lateral flow apparatus used to detect albumin includes: (a) a support structure defining a flow path; (b) a labeling reagent comprising an anti-albumin antibody as described above, the labeling reagent impregnated within the support structure in a labeling zone; and (c) a capture reagent, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path. One preferred embodiment includes a capture reagent comprising anti-feline albumin antibody.

One embodiment of the present invention is a "dipstick" device which can detect microalbuminuria in animals. Dipsticks may be constructed in a variety of ways that partly depend on the way in which they will be used. They may be held directly in a sample (e.g., a urine stream), dipped directly in sample contained in a collection vessel, or have sample applied to a strip contained in a plastic cassette or platform. A preferred embodiment of the "dipstick" assay is an immunometric system, described in U.S. Pat. No. 5,656,502, issued on Aug. 12, 1997, to MacKay and Fredrickson, and U.S. Pat. No. 6,001,658, issued Dec. 14, 1999 to Fredrickson. Particularly preferred is an ImmunoDip™ device available from Diagnostic Chemicals Ltd., PEI, CA.

Non-immunological methods may also be used. In order to detect microalbuminuria, methods such as preconcentration of the urine in order to concentrate albumin may be used to increase sensitivity of the test to protein. Such non-immunological methods include, for example, urine electrophoresis, where detection of microalbuminuria can be determined by methods known in the art, and include, for example, protein staining. In another embodiment, a protein based albumin test may be used to determine microalbuminuria on a preconcentrated sample of urine from an animal.

Once the albumin level has been measured, an assessment of whether early renal disease is present can then be made. Assessing the presence of early renal disease means comparing the level of albumin in the test sample to the level found in healthy animals. The presence of microalbuminuria in the sample, in the absence of changes in renal function, is indicative of early renal disease. As used herein, the term "indicative of early renal disease" means sufficient renal dysfunction is present to allow albumin to pass into the urine in the range of from about 10 μg/ml to about 300 μg/ml as measured when the specific gravity of the sample is 1.010. The amount of albumin present in the sample may vary depending on the amount of damage present but in early renal disease, the albumin level is higher than that found in healthy animals but lower than that detectable by current methods used to measure proteinuria. In the present invention, a determination of early renal disease is made when the level of albumin in the sample is determined to be in the range of from about 10 μg/ml to about 300 μg/ml. The level of albumin in the sample can also vary depending on the severity of the damage to the kidney. Preferred embodiments of the present inventions can detect albumin when about 10% or less, about 20% or less, about 30% or less, about 40% or less, about 50% or less, about 60% or less, or less than about 70% of kidney function is lost. Preferably, microalbuminuria is detected in time for medical intervention which may then delay or prevent the onset of late-stage renal disease. Such intervention may, for example, include, but is not limited to, the use of pharmacological compounds or dietary modifications to delay or prevent the progression of renal disease.

The methods of the present invention can be used to detect nephropathy in a canid, felid, equid, or other animal, particularly when the nephropathy is glomerulonephropathy, and especially glomerulonephritis. More specifically, the microalbuminuria measurement is correlated to the presence of early renal disease in a target animal. As used herein, the term "nephropathy" and/or "renal disease" refers to any disease of the kidneys, and may include, for example, nephritis of the glomerular, tubular, or interstitial renal tissues.

Such early stage nephropathy can result from many different causes, including, for example, allergy, cancer, parasitic, viral, or bacterial infection of any tissue in the animal, exposure to renal toxins, immune-mediated diseases, such as systemic lupus erythematosus and vasculitis, malignancy, Vitamin D3 rodenticides, pyelonephritis, leptospirosis, urinary tract obstruction, chronic inflammatory disease, pyoderma, pancreatitis, prostatitis, immune-mediated diseases, dental disease, high blood pressure, periodontal disease, hyperthyroidism or diabetes. As used herein, an "infectious agent" is one that infects animals and include, but are not limited to, viruses, bacteria, fungi, endoparasites and ectoparasites. Examples of viral infectious agents include, but are not limited to, adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses, parvoviruses, rabies viruses, and reoviruses, as well as other cancer-causing or cancer-related viruses. Examples of bacterial infectious agents include, but are not limited to, *Actinomyces, Bacillus, Bacteroides, Bartonella, Bordetella, Borrelia, Brucella, Campylobacter, Capnocytophaga, Clostridium, Corynebacterium, Coxiella, Dermatophilus, Ehrlichia, Enterococcus, Escherichia, Francisella, Fusobacterium, Haemobartonella, Helicobacter, Klebsiella,* L-form bacteria, *Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus,* and *Yersinia.* Examples of fungal infectious agents include, but are not limited to, *Absidia, Acremonium, Altenaria, Aspergillus, Basidiobolus, Bipolaris, Blastomyces, Candida, Chlamydia, Coccidioides, Conidiobolus, Cryptococcus, Curvalaria, Epidermophlyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothix, Stemphylium, Trichophyton, Trichosporon,* and *Xylohypha.* Examples of protozoan parasite infectious agents include, but are not limited to, *Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma,* and *Trypanosoma.* Examples of helminth parasite infectious agents include, but are not limited to, *Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichubekkam, Trichostrongylus, Trichuris, Uncinaria,* and *Wuchereria.* Examples of ectoparasite infectious agents include, but are not limited to, fleas, ticks, including hard ticks and soft ticks, flies such as midges, mosquitoes, sand flies, black flies, horse flies, horn flies, deer flies, tsetse flies, stable flies, myiasis-causing flies and biting gnats, ants, spiders, lice, mites, and true bugs, such as bed bugs and kissing bugs.

The present invention may also be used to measure multiple analytes. Other analytes may be any analyte which can be detected in sample suitable for use in detecting early renal disease. Additional analytes can be used to detect, for example, infectious disease or inborn errors of metabolism.

The present invention also includes kits suitable for detecting animal albumin using the methods disclosed herein. Suitable means of detection include the techniques disclosed herein, utilizing compounds that bind feline albumin, such as, for example, an anti-feline albumin antibody. Such an albumin-binding compound can be conjugated to a detectable marker. In another embodiment a kit can comprise an unlabelled albumin-binding compound as well as labeled albumin-binding compounds or other binding molecules with or without detectable markers to enable detection of albumin. The kit can also contain associated components, such as, but not limited to, buffers, labels, containers, inserts, tubings, vials, syringes and the like.

The present invention is based on a surprising discovery that microalbuminuria in felids can be used as a marker to predict the development of renal disease. Conventional human microalbuminuria detection methods do not detect dog or cat microalbuminuria as described in the examples below.

The following examples are provided for the purposes of illustration and are not intended to limit the scope of the present invention.

EXAMPLE 1

Measurement of Microalbuminuria in Normal, CRF and ARF Dogs

Urine samples were collected from 134 canine patients at the Colorado State University Teaching Hospital. These samples included urine from normal dogs, dogs suffering chronic renal failure, dogs suffering acute renal failure, and proteinuric dogs without renal failure. Samples were frozen at −20° C. for at least 24 hours and then thawed prior to use. Albumin levels were quantified by a microradial immunodiffusion assay as described in McDonald, Weber & Thiele, "Construction and Use of a Template Block for Radial Immunodiffusion" *Anal Biochem* 186:165-168 (1990) using a commercial anti-albumin antibody (polyclonal rabbit anti-dog albumin, available from Nordic Immunology distributed by Accurate Chemical and Scientific Corp., Westbury, N.Y.). For this assay the antibody at 1.5% (vol/vol) was added to melted 0.75% (wt/vol) EEO agarose in PBS. Gels, at a thickness of 0.75 mm were poured between two glass plates. The gels were allowed to solidify and after one of the glass plates was removed, allowed to dry slightly. Acrylic blocks, described in McDonald et al., supra., were placed on the agarose and 5 μl sample or standard was placed in each well of the acrylic block. Samples were run either undiluted or if the resulting ring was too large to measure the sample was diluted and re-tested. The standard curve using dog albumin (dog albumin fraction V, available from Sigma, St. Louis, Mo.) was linear within the range of 10-100 μg/ml. The acrylic blocks were left on the agarose and the unit was placed in a moist chamber and incubated overnight at room temperature. The agarose gels were then soaked in distilled water for several hours to remove the excess protein from the gel, the gel was dried and then stained with Coomassie Brilliant Blue so that the precipitin rings could be readily visualized. The diameter of each ring was measured and the ring diameter from each sample was compared to the standard curve and the albumin concentration of each sample was calculated.

The advantage of using this system for measuring albumin in the urine is that this system is more sensitive that the traditional assay with wells cut into the gels. This increased sensitivity is related to the to the concentrated delivery of the antigen into a small area as opposed to the larger surface area created by the edges of a well cut into the agarose For this initial study, samples that had less than or equal to 50 μg/ml were deemed normal, samples that had levels between 51 and 300 μg/ml were deemed microalbuminuric, and those that had levels over 300 μg/ml were deemed macroalbuminuric. The results of this study are shown in Table 1.

TABLE 1

Urinary albumin levels in 134 canine urine samples

| Albumin Level | Number of Animals | Percentage |
|---|---|---|
| Normal (0-50 μg/ml) | 59 | 44% |
| Microalbuminuria (51-300 μg/ml) | 21 | 16% |
| Macroalbuminuria (>300 μg/ml) | 54 | 40% |

EXAMPLE 2

ELISA Quantification of Microalbuminuria

Rabbit anti-canine serum albumin IgG (anti-CSA IgG) is diluted to 375 ng/ml in coating buffer (50 mM $Na_2CO_2$/$NaCHO_3$, pH 9.6). The diluted anti-CSA IgG solution is added to a plate of MaxiSorp™ C8 Break-apart Microwells (Nunc Cat. # 473768) at 100 μl/well, covered and incubated overnight (16 to 24 hours) at 4° C. The plate is washed four times with phosphate buffered saline with 0.05% Tween 20 (PBS-T) in an automatic plate washer and blotted dry. Blocking buffer (StabilCoat™ available from Surmodics Cat. #SC01-1000) is added at 200 μl/well, covered and incubated at room temperature for at least 1 hour.

While blocking, the canine serum albumin (CSA) dilution series is prepared. First, the CSA is diluted to 120 ng/ml in assay diluent (0.1% casein hydrolysate in PBS-T). This solution is serially diluted (1 part to 1 part) to make 60 ng/ml, 30 ng/ml, 7.5 ng/ml, 3.75 ng/ml, and 1.875 ng/ml. The last 5 standards are used for the standard curve (30 ng/ml and less) along with a "zero" standard (assay diluent with no CSA). Each urine sample to be tested is diluted 1/500, 1/1000, 1/2000, 1/4000, 1/8000, 1/16000 and 1/32000 in assay diluent.

The plate is then washed four times in an automatic plate washer and blotted dry. The CSA standard and diluted urine sample are added at 100 μl/well of each to the test wells. Assay diluent is added to duplicate wells for background control. The plate is covered and incubated for 2 hours at room temperature. As previously, the plate is washed four times with PBS-T and blot dry.

Dilute biotin labeled goat anti-CSA IgG (Bethyl Laboratories, Cat. #E40-113)] to 125 ng/ml in assay diluent. Add 100 μl/well of diluted biotin labeled goat anti-CSA IgG to all test wells. Cover plate and incubate for 30 minutes at room temperature. As previously, wash the plate four times with PBS-T and blot dry.

Dilute horseradish peroxidase labeled streptavidin (KPL Cat.# 14-30-00) to 500 ng/ml (1/1000 dilution) in assay diluent and add to all test wells at 100 μl/well. Cover and incubate at room temperature for 30 minutes. As previously, wash the plate four times with PBS-T and blot dry.

Mix TMB microwell peroxidase 2 component system (KPL Cat.#50-76-03) solutions together at equal volumes and add 100 μl/well of the TMB mixture to all wells. Cover and incubate for 30 minutes at room temperature. The reaction is stopped by adding 100 μl/well of stop solution (1M.$H_3PO_4$) directly to the TMB in each well. Read the wells at 450 nm in a spectrophotometer. Average the values of all duplicate wells, if any, and subtract background value from all the test values. Generate a standard curve from the standard values and generate a regression line ($r^2$>0.95). Using the regression formula, compute the CSA (ng/ml) value for each sample and multiply this value by the dilution factor. Only those values that fall in the linear portion of the standard curve should be used.

EXAMPLE 3

Use of the ImmunoDip™ Stick for the Detection of Microalbuminuria in Canine Urine Three ImmunoDip™ sticks (product number 700-01) for the detection of microalbuminuria in humans, were obtained from Diagnostic Chemicals Limited, Charlottetown, Prince Edward Island, Canada. Two canine urine samples (numbered 1086 and 1098) were selected from a group of samples obtained from dogs at the Colorado State University Veterinary Teaching Hospital, Fort Collins, Colo. Samples 1086 and 1098 were selected based on their albumin-levels as determined by an in-house ELISA to detect microalbuminuria in dogs. Sample 1086 was a negative sample, and sample 1098 had an albumin concentration of 221 μg/ml. For a positive control, approximately 50 μl of human blood was added to 5 ml deionized water Measurement of albumin in the urine was performed following the manufacturer's directions. Briefly, 3 ml of urine or the blood-spiked water was added to a test tube. The ImmunoDip stick was removed from the pouch and placed in the test tube containing the urine making sure the fluid level was above the vent hole in the device. The device was left in the sample for a minimum of 3 minutes after which it was removed and read by comparing the relative intensities of the two bands according to the interpretation-of-results insert that accompanies the test kit. The results of the in-house ELISA and the ImmunoDip tests are shown in Table 2.

TABLE 2

ImmunoDip ™ stick for microalbuminuria results

| Sample | In-House ELISA | ImmunoDip |
|---|---|---|
| 1086 | 0 μg/ml | Negative |
| 1098 | 221 μg/ml | Negative |
| Blood-spiked Water | Not-tested | Positive |

The limit of detection in the ImmunoDip test for human urine albumin is 12 μg/ml. Sample 1098 contained canine urine at a level significantly above this lower limit yet was negative for albumin by the ImmunDip™ test. These data suggest that this device does not recognize canine albumin, at least not in order to detect microalbuminuria.

EXAMPLE 4

Use of Micral® Test Strips for the Detection of Microalbuminuria in Canine Urine Fourteen Micral® urine test strips (product number 417146) for the detection of microalbuminuria in humans, were obtained from Roche BMC, Indianapolis, Ind. Thirteen canine urine samples were selected from a group of samples obtained from employee's dogs. Samples for use were selected based on their albumin-levels as determined by an in-house ELISA to detect microalbuminuria in dogs. Samples 2A, 4A &16 A were negative samples while the remaining samples had albumin concentrations ranging in value from 31.3 to >650 μg/ml. As a positive control, 50 μl of human blood was added to 5 ml deionized water.

Measurement of albumin in the urine was performed following the manufacturer's directions. Briefly, each dog's urine was collected in a sample collection cup. In addition, blood-spiked water was placed in a test tube. The Micral® stick was removed from the vial and placed in the collection cup (or test tube containing the blood-spiked water) making sure the fluid level was above the devices two black lines in each case. The device was left in sample for 5 seconds, removed and allowed to sit horizontally for 1 minute. The result was determined by comparing the color of the test pad to the color scale on the vial in accordance with the result insert that accompanied the test. The results of the in-house ELISA and the Micral® test are shown in Table 3.

The detection limit in the Micral® test for human albumin is about 20 μg/ml. Several samples contained canine albumin levels significantly above this lower limit yet were negative for albumin by the Micral® test. These data suggest that this device does not recognize canine urine albumin, at least not in order to detect microalbuminuria.

TABLE 3

Micral ® urine test strip results

| Sample | In-house ELISA | Micral ® |
|---|---|---|
| 1A | 79.4 μg/ml | Negative |
| 2A | 3.9 μg/ml | Negative |
| 4A | 5.9 μg/ml | Negative |
| 5A | 35.9 μg/ml | Negative |
| 9A | 48.6 μg/ml | Negative |
| 15A | 69.4 μg/ml | Negative |
| 16A | 8.3 μg/ml | Negative |
| 29A | 119.1 μg/ml | Negative |
| 86A | 31.3 μg/ml | Negative |
| 87A | 65.2 μg/ml | Negative |
| 14 | >650 μg/ml | Negative |
| 19 | Positive | Negative |
| 45 | 650 μg/ml | Negative |
| Blood-spiked water | Not tested | Positive |

EXAMPLE 5

Use of the ImmunoDip™ Stick for the Detection of Microalbuminuria in Canine Urine Fourteen ImmunoDip™ sticks (product number 700-01) for the detection of microalbuminuria in humans, were obtained from Diagnostic Chemicals Limited, Charlottetown, PE, Canada. Thirteen canine urine samples were selected from a group of samples obtained from dogs that were apparently normal. Samples for use were selected based on their albumin levels as determined by an in-house ELISA to detect microalbuminuria in dogs. Samples 2A, 4A &16 A were negative samples while the remaining samples had albumin concentrations ranging in value from 31.3 to >650 μg/ml. As a positive control, 50 μl of human blood was added to 5 ml deionized water.

Measurement of albumin in the urine was performed following the manufacturer's directions. Briefly, 3 ml of urine or the blood-spiked water was added to a test tube. The ImmunoDip stick was removed from the pouch and placed in the test tube containing the urine making sure the fluid level was above the device's vent hole in each case. The device was left in the sample for a minimum of 3 minutes after which, it was removed and read by comparing the relative intensities of the two bands according to the interpretation-of-results insert that accompanies the test kit. The results of the in-house ELISA and the ImmunoDip tests are shown in Table 4.

TABLE 4

ImmunoDip ™ Stick for Microalbuminuria results

| Sample | In-house ELISA | ImmunoDip ™ |
|---|---|---|
| 1A | 79.4 μg/ml | Negative |
| 2A | 3.9 μg/ml | Negative |
| 4A | 5.9 μg/ml | Negative |
| 5A | 35.9 μg/ml | Negative |
| 9A | 48.6 μg/ml | Negative |
| 15A | 69.4 μg/ml | Negative |
| 16A | 8.3 μg/ml | Negative |
| 29A | 119.1 μg/ml | Negative |
| 86A | 31.3 μg/ml | Negative |
| 87A | 65.2 μg/ml | Negative |
| 14 | >650 μg/ml | Negative |
| 19 | Positive | Negative |
| 45 | 650 μg/ml | Negative |
| Blood-spiked water | Not tested | Positive |

The detection limit in the ImmunoDip™ test for human albumin is about 20 μg/ml. Several samples contained canine albumin levels significantly above this lower limit yet were negative for albumin by the ImmunoDip™ test. These data suggest that this device does not recognize canine urine albumin, at least not in order to detect microalbuminuria.

EXAMPLE 6

Use of Micral®Test Strips for the Detection of Microalbuminuria in Canine Urine

Five Micral® urine test strips (product number 417146) for the detection of microalbuminuria in humans were obtained from Roche BMC, Indianapolis, Ind. Thirteen canine urine samples were selected from a group of samples obtained from dogs that were apparently normal. Samples for use were selected based on their albumin-levels as determined by an in-house ELISA to detect microalbuminuria in dogs. Samples 7 and 12 were negative samples while samples 14 and 25 had albumin levels of 621 μg/ml and >650 μg/ml, respectively. As a positive control, 50 μl of human blood was added to 5 ml deionized water.

Measurement of albumin in the urine was performed following the manufacturer's directions. Briefly, each dog's urine was collected in a sample collection cup. For the positive control, blood-spiked water was placed in a test tube. The Micral® stick was removed from the vial and placed in the collection cup (or test tube containing the blood-spiked water) making sure the fluid level was above the devices two black lines in each case. The device was left in sample for 5 seconds, removed and allowed to sit horizontally for 1 minute. The result was determined by comparing the color of the test pad to the color scale on the vial in accordance with the result insert that accompanied the test. The results of the in-house ELISA and the Micral® test are shown in Table 5.

TABLE 5

| Micral ® urine test strip results | | |
|---|---|---|
| Sample | In-House ELISA | Micral ® |
| 7 | 2.1 μg/ml | Negative |
| 12 | 0.8 μg/ml | Negative |
| 14 | 621 μg/ml | Negative |
| 25 | >650 μg/ml | Negative |
| Blood-spiked water | Not tested | Positive |

The limit of detection in the Micral® test for human urine albumin is about 20 μg/ml. Samples 14 and 25 contained canine albumin levels significantly above these lower levels yet were negative for albumin by the Micral® test. These data suggest that this device does recognize canine urine albumin, at least not in order to detect microalbuminuria.

EXAMPLE 7

Prevalence of Microalbuminuria in Dogs

For this study, two separate populations were examined. One sample population was derived from clinically normal dogs (n=86). The second sample population was derived from Colorado State University Teaching Hospital patients (n=150) presented for routine health screening, elective procedures, as well as evaluation of health problems. Microalbuminuria was quantitated using an antigen capture ELISA. The results of this measurement were normalized to a specific gravity of 1.010 to account for varying urine concentrations. Albumin in the urine of the hospital patients was also tested using Petstix 8™ urine protein test strips (Idexx Cat.# 98-06959-00).

Of the 86 clinically normal dogs, 68 (79%) had normalized albumin concentrations <1.0 mg/dL, 16 (19%) had normalized albumin concentrations >1.0 mg/dL and <30.0 mg/dL, and 2(2%) had normalized albumin concentrations >30.0 mg/dL. Of the 159 hospital patients, 112 (70%) were urine test strip negative and 51 of the 112 (46%) test-strip negative samples had normalized albumin concentrations >1.0 mg/dL. Conversely, 19 of 80 (24%) of samples with <1.0 mg/dL albumin were positive on urine test strip (see Table 6).

TABLE 6

| Normalized Urine Albumin Concentrations | Urine Protein Test Strip Result (n = 159) | | | |
|---|---|---|---|---|
| (# of samples) | Neg. (112) | Trace (20) | 1+ (15) | 2-4+ (12) |
| <1.0 mg/dL (80) | 61 (54%) | 12 (60%) | 5 (33%) | 2 (17%) |
| >1.0 and <30.0 mg/dL (58) | 49 (44%) | 6 (30%) | 2 (13%) | 1 (8%) |
| >30.0 mg/dL (21) | 2 (2%) | 2 (10%) | 8 (53%) | 9 (75%) |

In the two populations examined, prevalence of microalbuminuria (>1.0 mg/dL and <30.0 mg/dL) ranged from 19% to 36%. From these results, it appears microalbuminuria is prevalent in a significant number of dogs. Furthermore, use of commercially available urine protein test strips for the detection of albuminuria yields a substantial number of false positive results.

EXAMPLE 8

Purification of Canine Serum Albumin

This Example discloses a method for producing canine serum albumin. Canine serum was adjusted to 50% (w/v) ammonium sulfate, the solution rocked for 3 hours at 4° C., and the insoluble material precipitated by centrifugation at 10,000× g for 30 minutes. The supernatant was removed and dialyzed into 25 mM Tris, pH 8.0. The soluble material was loaded onto a pre-equilibrated, Hi-Trap Q-Sepharose column (Pharmacia, Peapack, N.J.) and the proteins eluted using a linear gradient of 0 to 1.0 M NaCl over 25 column volumes (CV). Collected fractions were analyzed by SDS-PAGe and fractions containing canine albumin were pooled and stored until needed. Using this method, 414 mg of albumin was purified from 20 ml of canine serum. Protein sequencing confirmed the purified protein was canine albumin.

EXAMPLE 9

Production of Anti-Canine Albumin Antibodies

This example discloses the method used to produce monoclonal antibodies (Mabs) TNB1, TNB2, TNB3, TNB4, TNB5, TNB6 which recognize canine serum albumin (CSA).

Balb/C mice were immunized by subcutaneous injection with Complete Freunds Adjuvant mixed with either 25 μg, 50 μg or 100 μg of canine serum albumin (available from Sigma, St. Louis, Mo.). After four weeks, blood samples were obtained and anti-CSA antibody titers determined by ELISA. Based on this data, the three mice immunized with 100 μg of CSA were chosen for further use in producing hybridomas. Two of these mice were given intravenous (IV) injections containing 100 μg of CSA and the third mouse received 100 μg intraperitoneally. Three days later, the mice were euthanized, the spleens removed and depleted of T-cells and the spleen cells fused with SP2/0 mouse myeloma cells following standard protocols. Individual hybridoma colonies were tested for the production of MAbs which recognize CSA and positive colonies were expanded and dilution cloned until stable MAb secreting lines were established.

EXAMPLE 10

Production of Anti-Canine Albumin Antibodies Using Subtractive Hybridization

This Example discloses procedures utilizing subtractive hybridization techniques to produce monoclonal antibodies (Mabs) which recognize canine serum albumin (CSA).

Anti-canine CSA hybridoma cell lines were produced using the following, published method of subtractive hybridization. Balb/C mice were injected intraperitoneally with 1.0 mg of BSA Fraction V (available from Boehringer Manheim, Indianapolis, Ind.), followed by IP injections of cyclophosphamide (CY)(100 mg/kg) at 10 minutes, 24, and 48 hours post-BSA injection. This BSA/CY treatment was repeated two weeks later. After another two weeks, the mouse was given a subcutaneous (SC) injection containing 100 μg of CSA (produced as described in Example 8) mixed with Complete Freunds Adjuvant. After an additional two weeks had passed, blood samples were obtained and serum antibody titers against CSA and BSA were determined by ELISA. A second injection of CSA (100 μg) was then given intraperitoneally to boost the animals anti-CSA antibody titers. Two weeks later, the mouse was given an intravenous (IV) injection of CSA (50 μg) and after three days, the mouse was sacrificed, its splenocytes harvested and fused with mouse SP2/0 myeloma cells using polyethylene glycol (PEG) following standard procedures. Individual hybridoma colonies were tested for the production of MAbs which recognize CSA and positive colonies were expanded and dilution cloned until stable MAb secreting lines were established. This procedure resulted in the production of hybridoma lines H398 and H399.

In addition to the hybridoma cells lines produced by the above procedure, the following modified subtractive hybridization procedure was used to produce additional anti-CSA hybridoma cell lines. 30 μg of CSA (produced as described in Example 8) were injected into the footpad of a Balb/C mouse. Three months later, the mouse was given an intraperitoneal (IP) injection containing 30 μg of CSA. Four months after the IP injection, the mouse was given a second IP injection containing 1.0 mg of BSA, followed by IP injections of cyclophosphamide (CY)(100 mg/kg) at 10 minutes, 24, and 48 hours post-BSA injection. After two weeks, this BSA/CY treatment was repeated and after two more weeks had elapsed, the mouse was given a subcutaneous (SC) injection of CSA (100 μg) mixed with complete Freunds adjuvant. After another two weeks, blood samples were obtained and serum antibody titers against CSA and BSA were determined by ELISA. The mouse was then given an intravenous (IV) injection of CSA (50 μg) and three days later, the mouse was euthanized, its splenocytes harvested and fused with mouse SP2/0 myeloma cells using polyethylene glycol (PEG) following standard procedures. Individual hybridoma colonies were tested for the production of MAbs which recognize CSA and positive colonies were expanded and dilution cloned until stable MAb secreting lines were established. This protocol resulted in the production of hybridoma cell lines H384, H385, H386, H387, H388, H389, H390, H391, H392, H393, H394, H395, H396, H400, H401 and H402.

EXAMPLE 11

Detection of Canine Serum Albumin by ELISA

This example discloses the use of a solid-phase ELISA to test the ability of the anti-canine serum albumin (CSA) antibodies to detect CSA.

The wells of a microtiter plate were coated with CSA (50 μg/well) (produced as described in Example 8) in carbonate buffer (50 mM carbonate/bicarbonate, pH 9.6) and the plate stored overnight at 4° C. The following day, excess liquid was removed, the plate blotted dry, and 150 μl of Blocking buffer (0.1% casein in PBS containing 0.05% Tween-20) were added to each well. The plate was incubated at room temperature (RT) for 30 minutes, after which, the Blocking buffer was removed and 50 μl of hybridoma supernatant (either undiluted or diluted in blocking buffer) were added to each well. Following a one hour incubation at RT, the wells were washed twice using Wash buffer (PBS containing 0.05% Tween-20), 50 μl of HRP-conjugated, goat, anti-mouse IgG and IgM (available from KPL Labs, Gaithersburg, Md.) were added to each well and the plate incubated at RT for 30 minutes. The wells were washed twice with Wash buffer, and 50 μl of TMB Substrate System (available from KPL Labs) were added to each well. The plate was incubated at RT for 10 minutes after which, the reaction was stopped by the addition of 50 μl of 2N sulfuric acid to each well. The plate was read at 450 nM using an ELISA plate reader and the results are shown below in Table 7.

TABLE 7

| Antibody | Undiluted | 1:10 | 1:100 |
|---|---|---|---|
| TNB1 | 1288 | 852 | 326 |
| TNB3 | 1242 | 1263 | 922 |
| TNB4 | 1449 | 1431 | 1546 |
| TNB5 | 1528 | 1585 | 1478 |
| TNB6 | 1782 | 1436 | 1103 |
| H386 | 1274 | 1273 | 1187 |
| H387 | 1394 | 1369 | 1326 |
| H388 | 1485 | 1529 | 1408 |
| H389 | 1685 | 1646 | 1265 |
| H390 | 1558 | 892 | 250 |
| H391 | 1490 | 1325 | 916 |
| H393 | 1744 | 1603 | 1640 |
| H394 | 435 | 955 | 577 |
| H395 | 1265 | 1049 | 1001 |
| H396 | 1564 | 1773 | 1390 |
| H397 | 49 | 59 | 48 |
| H398 | 1822 | 1641 | 1501 |
| H399 | 775 | 144 | 64 |
| H400 | 1572 | 1610 | 1239 |
| H401 | 1839 | 1683 | 1511 |
| H402 | 1799 | 1752 | 1447 |

EXAMPLE 12

Detection of Albumin From Several Species by ELISA

This example demonstrates the ability of three anti-canine albumin monoclonal Abs to recognize bovine (BSA), canine (CSA), equine (HSA) or human (HuSA) serum albumin by ELISA using the protocol outlined in Example 11 with the exception the wells were coated with 3× serial dilutions (from 5 μg/ml to 0.002 g/ml) of the indicated albumin. In addition, 10 μg of the indicated antibody was used in each well. The results are shown in Table 8.

TABLE 8

| Albumin Concentration | Coat Protein | | | |
|---|---|---|---|---|
| (μg/ml) | BSA | CSA | HSA | HuSA |
| | | TNB3 | | |
| 5 | .62 | 3.53 | 1.67 | .12 |
| 1.667 | .52 | 3.50 | 1.37 | .15 |
| .556 | .43 | 3.51 | .87 | .17 |
| .185 | .57 | 3.43 | .34 | .16 |
| .062 | .20 | 3.14 | .19 | .15 |
| .021 | .17 | 2.08 | .16 | .16 |
| .007 | .17 | .35 | .13 | .13 |
| .002 | .11 | .20 | .09 | .10 |
| | | TNB6 | | |
| 5 | .18 | 3.68 | .90 | 1.69 |
| 1.667 | .42 | 3.59 | .69 | .78 |
| .556 | .30 | 3.59 | .52 | .47 |
| .185 | .24 | 3.43 | .32 | .23 |
| .062 | .22 | 3.17 | .26 | .26 |
| .021 | .21 | 2.36 | .22 | .22 |
| .007 | .20 | 1.18 | .21 | .22 |
| .002 | .22 | .55 | .21 | .23 |
| | | H402 | | |
| 5 | .41 | 3.41 | .87 | .97 |
| 1.667 | .40 | 3.35 | .71 | .59 |
| .556 | .38 | 3.31 | .57 | .41 |
| .185 | .35 | 3.23 | .42 | .37 |
| .062 | .32 | 2.98 | .36 | .34 |
| .021 | .35 | 2.10 | .32 | .31 |
| .007 | .35 | 1.20 | .18 | .31 |
| .002 | .35 | .65 | .32 | .33 |

This data demonstrates mAb's TNB3, TNB6 and H402 have a much greater affinity for CSA as compared with BSA, HSA or HuSA.

EXAMPLE 13

Competition ELISA Using the Anti-Albumin mAb's H402, TNB3 and TNB6

This example compares the ability of the H402, TNB3 and TNB6 monoclonal antibodies to compete for binding to canine serum albumin (CSA). Competition between antibodies was measured by coating an entire ELISA plate with CSA, adding a labeled primary antibody to all the wells of the plate and then measuring the ability of several unlabeled antibodies to compete with the primary antibody for binding to the CSA. (All primary antibodies were labeled using biotin available from Pierce Chemical, Rockford, Ill. according to the manufacturers instructions). In this manner, each plate was used to test the ability of a single primary antibody to compete with two other anti-albumin antibodies for the ability to bind CSA. In addition, antibody raised against the extracellular domain of human high affinity IgE receptor alpha chain (anti-FceRIα) was used on each plate as a negative control. The details of the assay are as follows:

Three ELISA plates were coated overnight at 4° C. with CSA at 1 μg/ml. The following day, the wells were washed using Wash buffer (PBS+0.05% Tween-20) and blocked with Blocking Solution (STABILCOAT® IMMUNOASSAY STABILIZER; available from SurModics, Inc., Eden Prairie, Minn.) according to the manufacturer's directions. The wells were then washed using Wash buffer, and 100 μl of a single, labeled, primary antibody, either H402 at 20 ng/ml, TNB3 at 8 ng/ml or TNB6 at 12 ng/ml (concentrations were adjusted using Dilution buffer (0.1% casein in PBS+0.05% Tween-20)) were added to all of the wells of an individual plate so that each plate held a different primary antibody. To one row of wells on each plate was then added 100 μl of unlabeled secondary antibody, either H402, TNB3, TNB6 or anti-HuFCϵR1 at 20 μg/ml. Two-fold serial dilutions were then performed, diluting each secondary antibody across the plate so that the final concentrations of secondary antibody were from 10 ug/ml to 9 ng/ml. The plates were incubated at room temperature (RT) for 2 hours, washed with Wash buffer and 100 μl of horse-radish-peroxidase conjugated Streptavidin (diluted 1:1000 in Dilution buffer) were added. Following a 1 hour incubation at RT, the wells were washed with Wash buffer and 100 μl of developing solution (TMB Substrate; available from KPL Labs, Gaithersburg, Md.) were added to each well. After a 30 minute RT incubation, the plates were read at 450 nm using an ELISA plate reader. The results of this assay are shown below in Table 9.

TABLE 9

| Antibody Concentration (ng/ml) | Competing (secondary) Antibody | | | |
|---|---|---|---|---|
| | H402 | TNB3 | TNB6 | Anti-HuFCER1 |
| | H402 as Primary Antibody | | | |
| 10000 | .069 | 2.292 | .087 | 2.584 |
| 5000 | 0.164 | 2.328 | 0.195 | 2.576 |
| 2500 | 0.271 | 2.341 | 0.300 | 2.551 |
| 1250 | 0.517 | 2.275 | 0.559 | 2.569 |
| 625 | 1.212 | 2.255 | 1.093 | 2.592 |
| 312.5 | 2.104 | 2.262 | 1.683 | 2.540 |
| 156.25 | 2.548 | 2.293 | 2.239 | 2.557 |
| 78.125 | 2.670 | 2.381 | 2.402 | 2.512 |
| 39.06 | 2.752 | 2.461 | 2.514 | 2.518 |
| 19.53 | 2.765 | 2.427 | 2.655 | 2.660 |
| 9.77 | 2.798 | 2.657 | 2.611 | 2.639 |
| 0 | 2.710 | 2.641 | 2.577 | 2.642 |
| | TNB3 as Primary Antibody | | | |
| 10000 | 2.295 | 0.090 | 2.290 | 2.479 |
| 5000 | 2.493 | 0.245 | 2.409 | 2.645 |
| 2500 | 2.445 | 0.395 | 2.247 | 2.508 |
| 1250 | 2.480 | 0.796 | 2.185 | 2.397 |
| 625 | 2.485 | 1.534 | 2.239 | 2.428 |
| 312.5 | 2.378 | 2.084 | 2.208 | 2.483 |
| 156.25 | 2.529 | 2.535 | 2.324 | 2.484 |
| 78.125 | 2.463 | 2.643 | 2.351 | 2.497 |
| 39.06 | 2.566 | 2.674 | 2.390 | 2.509 |
| 19.53 | 2.607 | 2.740 | 2.520 | 2.602 |
| 9.77 | 2.763 | 2.716 | 2.611 | 2.669 |
| 0 | 2.867 | 2.798 | 2.756 | 2.764 |
| | TNB6 as Primary Antibody | | | |
| 10000 | 0.122 | 2.307 | 0.134 | 2.490 |
| 5000 | 0.303 | 2.410 | 0.310 | 2.604 |
| 2500 | 0.459 | 2.177 | 0.473 | 2.569 |
| 1250 | 0.769 | 2.276 | 0.733 | 2.550 |
| 625 | 1.446 | 2.283 | 1.383 | 2.501 |
| 312.5 | 2.126 | 2.319 | 2.053 | 2.402 |
| 156.25 | 2.502 | 2.430 | 2.358 | 2.564 |
| 78.125 | 2.647 | 2.455 | 2.480 | 2.516 |
| 39.06 | 2.743 | 2.496 | 2.557 | 2.530 |
| 19.53 | 2.745 | 2.579 | 2.605 | 2.582 |
| 9.77 | 2.787 | 2.697 | 2.654 | 2.559 |
| 0 | 2.772 | 2.685 | 2.319 | 2.377 |

The data demonstrate that the monoclonal antibodies H402 and TNB6 compete for binding of canine serum albumin consistent with these antibodies sharing the same, or closely related, epitopes. The data further demonstrate that binding of canine serum albumin by TNB3 is unaffected by H402 or TNB6.

EXAMPLE 14

Binding of Canine and Feline Albumin by H352, H398 and TNB3

This example compares the ability of three anti-albumin antibodies (H352, H398 & TNB3) to bind canine (CSA) or feline (FSA) albumin.

The binding assay was performed as follows. To enable detection, horse-radish peroxidase (HRP) (Pierce Chemical, Rockford, Ill.) was conjugated to either CSA or FSA following manufacturer's protocol. The wells of a microtiter plate were coated with a range (from 10 μg/ml to 9.77 ng/ml) of antibody (either H352, H398 or TNB3) in carbonate buffer (50 mM carbonate/bicarbonate, pH 9.6) and the plates stored overnight at 4° C. The following day, excess liquid was removed and the wells were blocked using blocking solution (STABILCOAT® IMMUNOASSAY STABILIZER; available from SurModics, Inc., Eden Prairie, Minn.) following manufacturer's instructions. Following removal of the blocking solution, the wells were rinsed using Wash buffer (PBS containing 0.05% Tweeen-20) and HRP-FSA (diluted 1:400 in carbonate buffer) or HRP-CSA (diluted 1:800 in carbonate buffer) were added to the wells and the plate incubated at room temperature (RT) for 30 minutes. The HRP-albumin conjugate was removed, the wells washed twice using Wash Buffer and 50 μl of TMB Substrate System (available from KPL Labs, Gaithersburg, Md.) were added to each well. The plate was incubated at RT for 10 minutes after which the reaction was stopped by the addition of 50 μl of 2N sulfuric acid to each well. The plate was read at 450 nM using an ELISA plate reader. The results are shown below in Table 10.

TABLE 10

| | mAb | | | | | |
|---|---|---|---|---|---|---|
| MAb | H352 | | H398 | | TNB3 | |
| Concentration | Coat Protein | | | | | |
| (ng/ml) | FSA | CSA | FSA | CSA | FSA | CSA |
| 10000 | 4.200 | 4.184 | 2.984 | 3.887 | 0.055 | 4.191 |
| 5000 | 4.200 | 4.200 | 1.944 | 2.806 | 0.047 | 4.184 |
| 2500 | 4.189 | 4.160 | 1.532 | 2.333 | 0.049 | 4.177 |
| 1250 | 4.127 | 4.200 | 1.187 | 1.941 | 0.099 | 4.186 |
| 625 | 2.740 | 4.084 | 0.493 | 0.769 | 0.043 | 4.178 |
| 312.5 | 1.266 | 2.814 | 0.168 | 0.282 | 0.045 | 3.410 |
| 156.25 | 0.713 | 1.598 | 0.095 | 0.135 | 0.043 | 2.400 |
| 78.13 | 0.324 | 0.859 | 0.078 | 0.090 | 0.042 | 1.109 |
| 39.06 | 0.178 | 0.413 | 0.053 | 0.063 | 0.043 | 0.543 |
| 19.53 | 0.107 | 0.236 | 0.047 | 0.055 | 0.049 | 0.309 |
| 9.77 | 0.077 | 0.132 | 0.050 | 0.051 | 0.059 | 0.191 |
| 0 | 0.044 | 0.048 | 0.048 | 0.061 | 0.049 | 0.048 |

The data monoclonal antibody H352 binds to both FSA and CSA with roughly equal affinity. Monoclonal antibody H398 also recognizes both FSA and CSA although it has greater affinity for CSA. Finally, the data demonstrates that monoclonal antibody TNB3 binds specifically binds to CSA and does not bind FSA.

EXAMPLE 15

Albumin in Canines Suffering Heartworm-Induced Renal Disease

This example discloses the albumin levels present in the canine *Dirofilaria immitis*-induced nephropathy. In this model, animals are infected with *D. immitis* which results in renal damage due to antigen-antibody-complex induced damage of the glomerulus as described in Grauer, G. F., et. al., *American Journal or Tropical Medicine and Hygiene;* 39(4), 1988, p380-387. It is known in this model that *D. immitis* antigen appears in the blood approximately seven-months post-infection. For this example, animals were infected with *D. immitis* and urine samples collected monthly by catheterization. It should be noted that in some cases, the process of catheterization can result elevated albumin levels; as a result, animals were only considered positive for microalbuminuria when they were found to be microalbuminuric in two consecutive samples. The amount of albumin in each sample was determined using an ELISA assay. The results are shown below in Table 11. Boxes labeled N/A indicate where no sample was available.

TABLE 11

| Months | Animal Identifier | | | | | | | | | | | |
|---|---|---|---|---|---|---|---|---|---|---|---|---|
| Post Infection | HOP (A) | IGH (A) | POR (A) | SSH (A) | XTJ (A) | YOH (A) | AXH (B) | CAH (B) | FVH (B) | GUH (B) | HOH (B) | VIP (B) |
| | 174.9 | 0.2 | 2.3 | 1.9 | 0.3 | 2.9 | 8.0 | 72.6 | 0.3 | 3.7 | 4.2 | 2.1 |
| 1 | 2.1 | 3.8 | 2.4 | 0.3 | N/A | 8.7 | 4.0 | 4.0 | | 3.7 | 0.2 | 0.4 |
| 2 | 33.8 | 2.0 | 9.5 | 2.4 | 29.9 | N/A | 3.3 | 0.2 | 3.0 | 3.3 | 0.9 | 2.6 |
| 4 | 1.3 | 16.4 | 0.3 | 3.0 | 0.3 | 0.3 | 3.7 | 22.7 | 2.5 | 2.3 | 1.8 | 5.4 |
| 5 | 2.2 | 4.2 | N/A | 2.0 | 18.1 | 4.2 | 3.4 | 3.0 | 0.3 | 1.9 | 0.2 | 4.1 |
| 6 | 4.9 | 9.9 | N/A | 2.5 | N/A | 0.3 | 0.2 | 2.6 | 2.7 | 1.5 | 0.4 | 0.4 |
| 7 | 1.4 | 48.1 | 0.3 | 0.3 | 20.7 | 45.6 | 3.9 | 0.3 | 1.9 | 20.7 | 3.3 | 8.1 |
| 8 | 8.4 | N/A | 18.0 | N/A | 60.6 | 16.2 | 3.1 | 4.8 | 6.5 | 2.8 | 8.5 | 15.4 |
| 9 | 26.2 | 2.9 | 4.4 | 0.4 | 46.8 | 16.1 | 6.0 | 0.3 | 24.6 | 3.6 | 0.3 | N/A |
| 10 | N/A | 11.0 | 3.4 | 10.8 | 26.2 | 15.7 | 13.1 | 21.3 | 54.0 | 60.3 | 0.2 | 46.0 |
| 11 | 52.1 | 125.7 | 43.5 | 36.9 | 180.6 | 67.8 | 3.9 | 27.3 | 11.5 | 6.5 | 59.5 | 736. |
| 12 | 58.5 | 16.2 | 22.2 | 52.9 | 51.3 | 54.9 | 6.8 | 76.2 | 23.4 | 5.9 | 97.4 | 167.2 |
| 13 | 113.5 | 56.4 | 25.1 | 8.1 | 132.4 | 112.7 | 14.7 | 30.1 | 327.2 | 13.3 | 65.5 | 132.6 |
| 14 | 134.3 | 60.2 | 132.1 | 16.8 | 123.0 | 82.9 | 66.6 | 65.8 | 500.0 | 5.0 | 285.7 | 69.06.1 |
| 15 | 206.0 | 4.0 | 122.0 | 23.7 | 39.1 | 18.6 | 3.8 | 16.4 | 500.0 | 8.0 | 107.8 | 34.8 |
| 16 | 37.3 | 7.6 | 500.0 | 5.4 | 52.5 | 10.1 | 5.5 | 17.8 | 500.0 | 4.9 | 43.1 | N/A |

TABLE 11-continued

| Months Post Infection | HOP (A) | IGH (A) | POR (A) | SSH (A) | XTJ (A) | YOH (A) | AXH (B) | CAH (B) | FVH (B) | GUH (B) | HOH (B) | VIP (B) |
|---|---|---|---|---|---|---|---|---|---|---|---|---|
| 17 | N/A | 45.2 | N/A | 8.6 | 181.6 | 89.1 | 30.9 | 19.8 | 500.0 | 16.4 | 53.0 | N/A |
| 18 | 18.8 | 112.1 | 211.1 | 5.4 | 70.4 | 26.8 | 10.5 | 14.9 | N/A | 5.4 | 21.3 | N/A |
| 19 | 16.7 | 67.0 | 176.7 | 12.1 | 208.4 | N/A | N/A | 36.3 | N/A | 4.9 | 57.1 | N/A |
| 20 | N/A | N/A | N/A | N/A | 500.0 | N/A | N/A | N/A | N/A | 1.9 | N/A | N/A |
| 21 | N/A | N/A | N/A | N/A | N/A | 37.9 | 9.2 | 41.7 | N/A | 11.0 | 17.1 | N/A |
| 22 | 1.6 | 4.7 | 75.8 | 9.1 | 500.0 | 27.2 | 22.2 | 500.0 | N/A | 3.2 | 46.2 | N/A |
| 23 | 83.2 | 37.6 | 30.3 | 17.5 | 500.0 | 60.3 | 54.3 | 500.0 | N/A | 5.2 | 37.7 | N/A |

The data demonstrate that following infection with *D. immitis,* there is a progressive increase in the level of albumin in the urine. Additionally, most animals became microalbuminuric within 1-2 months following the time of appearance of *D. immitis* antigen in the blood. Microalbuminuria could be detected in all animals by the end of the study.

EXAMPLE 16

Albumin Levels in Canines Suffering from Hereditary Nephritis

This example compares the level of microalbuminuria (MA) with a commonly used marker for renal disease, the urinary protein/ creatinine (UP/C) ratio, over time in animals suffering from hereditary nephritis (HD). In this model, the animals carry a genetic defect which results in the rapid development of renal disease during the course of the animals life as described in Lee, G E, *American Journal of Veterinary Research,* 1999: 60, p373-383. In this example, urine was periodically collected from a colony of normal dogs and a colony of dogs suffering HD. The amount of albumin in each sample was determined using an ELISA assay. In addition, the urinary protein/creatinine UP/C) ratio was determined using veterinary reference lab. By this measurement, renal disease is considered to be present when the UP/C ratio is greater than 1.0. The results of this study are shown below in Table 12.

TABLE 12

| | Animal Identification | | | | | | | | | |
|---|---|---|---|---|---|---|---|---|---|---|
| | Fonzi (control) | | Jake (control) | | Ned (control) | | Oscar (control) | | Pete (control) | |
| Age (weeks) | UP/C Ratio | MA (μg/ml) | UP/C Ratio | MA | UP/C Ratio | MA (μg/ml) | UP/C Ratio | MA (μg/ml) | UP/C Ratio | MA (μg/ml) |
| 8 | 0.1 | 2 | 1.6 | 0 | 0.2 | 5 | 0.6 | 2 | 0.9 | 3 |
| 11 | 0.2 | 2 | 0.7 | 5 | 0.2 | 5 | 0.2 | 8 | 0.3 | 4 |
| 13 | 0.3 | 1 | 0.3 | 0 | 0.2 | 5 | 0.9 | 3 | 0.4 | 2 |
| 15 | 1.0 | 3 | 0.6 | 6 | 0.2 | 5 | 0.3 | 4 | 0.2 | 2 |
| 17 | 0.2 | 1 | 0.2 | 3 | 0.2 | 5 | 0.1 | 3 | 0.2 | 6 |
| 19 | 0.4 | 15 | 0.5 | 4 | 0.2 | 5 | | | 0.1 | 3 |
| 21 | 0.1 | 4 | 1.0 | 7 | 0.2 | 5 | 0.1 | 2 | 0.1 | 1 |
| 23 | 0.3 | 0 | 0.2 | 3 | 0.2 | 5 | 0.2 | 1 | 0.1 | 1 |
| 25 | 0.6 | 1 | 0.1 | 6 | 0.2 | 5 | 0.1 | 1 | 0.1 | 20 |
| 27 | 0.1 | 1 | 0.2 | 6 | 0.2 | 5 | 0.1 | 0 | 0.1 | 6 |
| 30 | 0.1 | 2 | 0.1 | 4 | 0.2 | 5 | 0.1 | 2 | 0.0 | 1 |
| 34 | 0.2 | 220 | 0.1 | 4 | 0.2 | 5 | 0.1 | 1 | 0.1 | 2 |
| 38 | 0.1 | 1 | 0.1 | 2 | 0.2 | 5 | 0.1 | 1 | 0.1 | 4 |

| | Animal Identification | | | | | | | | | |
|---|---|---|---|---|---|---|---|---|---|---|
| | Ethan (HN) | | Frasier (HN) | | Greg (HN) | | Ike (HN) | | Lester (HN) | |
| Age (weeks) | UP/C Ratio | MA (μg/ml) | UP/C Ratio | MA (μg/ml) | UP/C Ratio | MA (μg/ml) | UP/C Ratio | MA (μg/ml) | UP/C Ratio | MA (μg/ml) |
| 8 | 0.2 | 4 | 0.1 | 6 | 0.1 | 2 | 1.0 | 6 | 0.8 | 10 |
| 11 | 0.3 | 9 | 0.2 | 4 | 0.1 | 4 | 0.2 | 10 | 0.4 | 8 |
| 13 | 0.6 | 4 | 0.2 | 1 | 0.3 | 2 | 0.2 | 1 | 0.5 | 12 |
| 15 | 0.5 | 8 | 0.3 | 12 | 0.1 | 12 | 0.7 | 7 | 0.3 | 3 |
| 17 | 0.1 | 17 | 0.6 | 358 | 0.2 | 487 | 1.0 | 557 | 0.4 | 7 |
| 19 | 1.0 | 82 | 2.3 | 314 | 0.4 | 2 | 4.4 | 918 | 0.6 | 115 |
| 21 | 3.0 | 136 | 1.1 | 30 | 0.2 | 2 | 6.6 | 1574 | 1.0 | 561 |
| 23 | 6.2 | 4954 | 5.1 | 2145 | 0.3 | 71 | 12.5 | 5560 | 3.0 | 615 |
| 25 | 10.1 | 744 | 9.0 | 3000 | 1.6 | 603 | 16.6 | 2920 | 3.7 | 17 |

TABLE 12-continued

| | | | | | | | | | | |
|---|---|---|---|---|---|---|---|---|---|---|
| 27 | 6.6 | 1179 | 7.3 | 2020 | 3.5 | 1499 | 15.3 | 3904 | 7.0 | 1477 |
| 30 | 15.7 | 2734 | 12.3 | 2696 | 5.7 | 1733 | 16.5 | 2276 | 9.3 | 1679 |
| 34 | 11.6 | 1901 | 12.9 | 2 | 8.2 | 309 | 4.4 | 3608 | 8.7 | 1992 |
| 38 | 6.4 | 3310 | 13.9 | 3597 | 8.8 | 4845 | 8.5 | 4465 | 8.1 | 1919 |

| | Animal Identification | | | | | | | | | |
|---|---|---|---|---|---|---|---|---|---|---|
| | Nate (HN) | | Newt (HN) | | Quark (HN) | | Quirt (HN) | | Eddie (HN) | |
| Age (weeks) | UP/C Ratio | MA (μg/ml) | UP/C Ratio | MA (μg/ml) | UP/C Ratio | MA (μg/ml) | UP/C Ratio | MA (μg/ml) | UP/C Ratio | MA (μg/ml) |
| 8 | 0.4 | 6 | 0.2 | 5 | 0.1 | 2 | 0.4 | 1 | 1.6 | 16 |
| 11 | 0.4 | 0 | 0.4 | 0 | 0.1 | 3 | 0.4 | 4 | 0.2 | 10 |
| 13 | 0.4 | 5 | 0.2 | 4 | 0.7 | 11 | 0.2 | 3 | 0.4 | 6 |
| 15 | 0.4 | 2 | 0.1 | 19 | 0.3 | 5 | 0.1 | 1 | 0.3 | 6 |
| 17 | 0.3 | 4 | 1.1 | 116 | 0.4 | 74 | 0.1 | 12 | 0.1 | 5 |
| 19 | 0.6 | 7 | 1.5 | 265 | 0.6 | 232 | 0.2 | 25 | 0.4 | 10 |
| 21 | 0.2 | 52 | 2.4 | 1321 | 2.8 | 620 | 0.6 | 267 | 1.2 | 1063 |
| 23 | 2.1 | 340 | 8.7 | 2665 | 9.2 | 1223 | 3.4 | 543 | 2.8 | 1307 |
| 25 | 2.2 | 622 | 9.6 | 4711 | 8.8 | 1938 | 4.6 | 1208 | 8.7 | 19471 |
| 27 | 3.2 | 483 | 10.1 | 1309 | 7.8 | 2007 | 9.1 | 3054 | 6.9 | 1052 |
| 30 | 5.8 | 1529 | 9.0 | 2989 | 14.1 | 3419 | 9.3 | 2747 | 13.9 | 3188 |
| 34 | 7.3 | 1483 | 8.8 | 1806 | 13.1 | 3055 | 9.9 | 6379 | 10.5 | 4927 |
| 38 | 8.9 | 2955 | 8.1 | 6487 | 12.2 | 3118 | 9.5 | 3044 | 12.7 | 6717 |

| | Animal Identification | | | | | | | | | |
|---|---|---|---|---|---|---|---|---|---|---|
| | Felix (HN) | | Fred (HN) | | Gus (HN) | | Neal (HN) | | Norm (HN) | |
| Age (weeks) | UP/C Ratio | MA (μg/ml) | UP/C Ratio | MA (μg/ml) | UP/C Ratio | MA (μg/ml) | UP/C Ratio | MA (μg/ml) | UP/C Ratio | MA (μg/ml) |
| 8 | 0.7 | 1 | 0.3 | 3 | 0.1 | 5 | 0.8 | 0 | 0.3 | 1 |
| 11 | 0.1 | 8 | 0.1 | 12 | 0.1 | 4 | 0.2 | 3 | 0.1 | 1 |
| 13 | 0.1 | 1 | 0.5 | 1 | 0.1 | 22 | 0.4 | 3 | 0.1 | 0 |
| 15 | 0.3 | 5 | 0.6 | 1 | 0.2 | 55 | 0.1 | 2 | 0.5 | 1 |
| 17 | 0.8 | 122 | 0.5 | 6 | 1.7 | 24 | 0.4 | 2 | 0.7 | 4 |
| 19 | 0.3 | 87 | 0.3 | 13 | 2.2 | 77 | 0.6 | 428 | 0.5 | 7 |
| 21 | 0.8 | 903 | 0.8 | 9 | 3.9 | 16 | 0.6 | 210 | 1.3 | 354 |
| 23 | 2.6 | 1679 | 0.6 | 81 | 9.3 | 1565 | 6.6 | 1335 | 5.7 | 1535 |
| 25 | 6.9 | 16170 | 1.9 | 152 | 6.4 | 3950 | 8.4 | 4091 | 9.5 | 3290 |
| 27 | 10.2 | 2452 | 3.5 | 11 | 5.2 | 1263 | 10.1 | 1158 | 5.5 | 798 |
| 30 | 12.0 | 2612 | 8.1 | 1887 | 8.3 | 2648 | 9.2 | 2523 | 6.8 | 2796 |
| 34 | 9.3 | 4146 | 7.1 | 3403 | 8.5 | 4583 | 10.1 | 1767 | 11.5 | 2603 |
| 38 | 10.4 | 6218 | 10.8 | 7141 | 7.9 | 3758 | 10.4 | 2906 | 7.0 | 3403 |

| | Animal Identification | | | | | | | | | |
|---|---|---|---|---|---|---|---|---|---|---|
| | Paul (HN) | | Quinn (HN) | | Scooter (HN) | | | | | |
| Age (weeks) | UP/C Ratio | MA (μg/ml) | UP/C Ratio | MA (μg/ml) | UP/C Ratio | MA (μg/ml) | UP/C Ratio | MA (μg/ml) | UP/C Ratio | MA (μg/ml) |
| 8 | 0.6 | 4 | 0.1 | 5 | 1.4 | | | | | |
| 11 | 0.1 | 8 | 0.1 | 1 | 0.2 | 3 | | | | |
| 13 | 0.4 | 1 | 0.2 | 5 | 0.3 | 7 | | | | |
| 15 | 0.2 | 0 | 0.2 | 1 | 0.1 | 21 | | | | |
| 17 | 0.1 | 6 | 0.1 | 3 | 0.3 | 66 | | | | |
| 19 | 0.7 | 6 | 0.6 | 5 | 2.7 | 323 | | | | |
| 21 | 0.1 | 58 | 0.1 | 16 | 4.3 | 20 | | | | |
| 23 | 1.3 | 206 | 0.6 | 29 | 8.8 | 2678 | | | | |
| 25 | 2.0 | 598 | 1.5 | 224 | 11.3 | 2957 | | | | |
| 27 | 4.2 | 674 | 2.1 | 431 | 10.1 | 3864 | | | | |
| 30 | 4.0 | 2650 | 5.4 | 1468 | 11.2 | 2118 | | | | |
| 34 | 5.5 | 0 | 10.0 | 1395 | 12.5 | 5098 | | | | |
| 38 | 6.4 | 4324 | 8.6 | 1624 | 8.4 | 3238 | | | | |

The data demonstrate that there is a progressive increase in microalbuminuria in animals suffering from hereditary nephritis. In addition, in virtually all animals, microalbuminuria was detected prior to the UP/C ration being greater than 1.0.

EXAMPLE 17

This Example discloses a method to purify feline serum albumin (FSA) from cat sera.

50 milliliters (ml) of cat sera was chilled in an ice bath to just above freezing and mixed with 100 ml of Precipitation Buffer I (10 mM sodium acetate, pH 4.0, 23.75% v/v ethanol) at a rate of 20 ml/minute with magnetic stirring. The mixture was chilled at −5° C. for 15 minutes and then subjected to centrifugation at 10,000 RPM for 10 minutes. The supernatant was removed and mixed with 10 ml of Precipitation II (250 mM zinc acetate, 19% v/v ethanol), chilled at −5° C. for 15 minutes and subjected to centrifugation at 10,000 RPM for 10 minutes. The supernatant was discarded and to the pellet was added 175 ml of Extraction Buffer (10 mM barium acetate, 27.3 mM acetate, 18% v/ ethanol). The mixture was stirred at −5° C. for 15 minutes and then centrifuged at 10,000 RPM for 10 minutes. The supernatant (S1) was removed and set aside. The pellet was extracted once more using 100 ml of Extraction Buffer as above and centrifuged at 10,000 RPM for 10 minutes. The supernatant (S2) was removed and pooled with supernatant S1 from the first extraction. The pooled supernatants were adjusted to pH 5.2 using 1 N HCl and applied to a DEAE column (25 ml bed volume) that had been pre-equilibrated with Buffer A (20 mM sodium acetate, pH 5.2). The column was washed with 50 ml of Buffer A, followed by a wash using 65 ml of Buffer B (25 mM sodium acetate, pH 4.5). The bound FSA was released from the column with 50 ml of Buffer C (150 mM sodium acetate, pH 4.0) and collected in 5 ml fractions. The fractions were analyzed on 14% PAGe reducing gels, fractions containing 66 kD proteins were pooled and 1/10th volume of 10× PBS (phosphate buffered saline) added. The pooled fractions were then applied to a Sephacryl S-200 column (2.6×65 cm) that had been pre-equilabrated with PBS and 5 ml fractions collected at 2.5 ml/minute. Fractions were analyzed using 14% PAGE reducing gels and fractions containing the 66 kD albumin protein were pooled. The purified albumin was then filter sterilized through a 0.2 μm filter.

EXAMPLE 18

This Example discloses the method used to produce monoclonal antibodies (Mabs) that recognize feline serum albumin (FSA).

Feline albumin, which was used as the antigen, was purified from pooled cat sera using the protocol given in Example 17. Two Balb/C mice were immunized by intraperitoneal injection with 100 μg of feline albumin in Freund's complete adjuvant. After two weeks, each mouse received a second intraperitoneal injection, containing 100 μg feline albumin in incomplete Freund's adjuvant. After an additional 17 days, each mouse received an intravenous injection of 25 μg feline albumin. Three days later, the splenocytes were harvested and fused with mouse SP2/0 myeloma cells at mid-log growth phase using the ClonaCell™-HY Hybridoma Cloning Kit (StemCell Technologies, Vancouver, BC; cat#28411). Cell fusions were performed according to the manufacturers instructions; all media was supplied by the manufacturer. Briefly, approximately $1\times10^8$ splenocytes and $2\times10^7$ SP2/0 cells were washed 3 times in RPMI media without serum. The cell pellet was then centrifuged in the presence of PEG. Following aspiration of the PEG, the cells were resuspended in recovery medium and incubated overnight. The following day, the cells were harvested by centrifugation, resuspended in a medium containing methylcellulose, and plated in 100 mm sterile petri dishes. After incubating for ten days, 960 macroscopically visible colonies were picked and each colony transferred to an individual well of a 96-well cell culture plate containing growth medium. The isolated colonies were incubated for 14 days after which time, each colony was screened for the production of anti-feline albumin antibody using the ELISA procedure given in Example 11, with the exception FSA was substituted for CSA. Colonies that were positive for anti-feline albumin antibody were expanded and cloned by limiting dilution until stable anti-feline albumin Mab secreting cell lines were identified. This procedure resulted in the production of the following nineteen monoclonal antibodies that bound feline albumin.

TABLE 13

| Antibody Identifier | Isotype |
|---|---|
| H419 | $IgG_1$ |
| H420 | IgM |
| H421 | IgM |
| H422 | $IgG_1$ |
| H423 | — |
| H424 | $IgG_{2a}$ |
| H425 | $IgG_{2a}$ |
| H426 | — |
| H427 | $IgG_{2a}$ |
| H428 | $IgG_1$ |
| H429 | $IgG_1$ |
| H430 | $IgG_{2a}$ |
| H431 | $IgG_1$ |
| H432 | IgM |
| H433 | $IgG_1$ |
| H434 | $IgG_1$ |
| H435 | $IgG_{2a}$ |
| H436 | $IgG_1$ |
| H437 | $IgG_1$ |

EXAMPLE 19

This Example demonstrates the ability of the anti-feline albumin antibodies to recognize either bovine serum albumin (BSA), equine serum albumin (HSA), canine serum albumin (CSA) or feline serum albumin (FSA) by ELISA, using the protocol given in Example 11 with the exception the wells were coated with albumin from the species indicated. The results of these assays are shown below in Table 14.

TABLE 14

| H-419 | | | | | H422 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 148 | 252 | 190 | 167 | 0.5 | 245 | 422 | 1211 | 567 |
| 0.125 | 143 | 237 | 187 | 97 | 0.125 | 184 | 329 | 715 | 330 |
| 0.0313 | 139 | 218 | 171 | 76 | 0.0313 | 143 | 258 | 369 | 156 |

TABLE 14-continued

| | | | | | | | | | |
|---|---|---|---|---|---|---|---|---|---|
| 0.0078 | 144 | 246 | 188 | 82 | 0.0078 | 139 | 231 | 219 | 95 |
| 0.0020 | 142 | 212 | 157 | 85 | 0.0020 | 111 | 208 | 151 | 75 |
| 0.0005 | 136 | 209 | 154 | 73 | 0.0005 | 122 | 219 | 174 | 72 |

| H-424 | | | | | H-425 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 177 | 301 | 266 | 830 | 0.5 | 308 | 512 | 568 | 1050 |
| 0.125 | 140 | 249 | 179 | 746 | 0.125 | 208 | 327 | 330 | 907 |
| 0.0313 | 131 | 224 | 152 | 666 | 0.0313 | 151 | 258 | 213 | 538 |
| 0.0078 | 145 | 236 | 165 | 340 | 0.0078 | 132 | 234 | 172 | 234 |
| 0.0020 | 135 | 226 | 157 | 158 | 0.0020 | 107 | 194 | 130 | 110 |
| 0.0005 | 125 | 234 | 144 | 90 | 0.0005 | 117 | 214 | 154 | 80 |

| H-427 | | | | | H-428 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 124 | 231 | 157 | 584 | 0.5 | 137 | 228 | 147 | 926 |
| 0.125 | 127 | 215 | 159 | 759 | 0.125 | 138 | 242 | 165 | 773 |
| 0.0313 | 135 | 227 | 148 | 462 | 0.0313 | 139 | 235 | 162 | 458 |
| 0.0078 | 128 | 222 | 164 | 227 | 0.0078 | 133 | 226 | 156 | 170 |
| 0.0020 | 142 | 227 | 145 | 113 | 0.0020 | 115 | 219 | 147 | 97 |
| 0.0005 | 133 | 232 | 148 | 79 | 0.0005 | 121 | 211 | 153 | 78 |

| H-430 | | | | | H-431 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 109 | 146 | 114 | 113 | 0.5 | 125 | 215 | 2153 | 1196 |
| 0.125 | 103 | 194 | 121 | 94 | 0.125 | 125 | 200 | 1954 | 1015 |
| 0.0313 | 109 | 193 | 122 | 75 | 0.0313 | 126 | 206 | 1501 | 481 |
| 0.0078 | 114 | 196 | 123 | 69 | 0.0078 | 124 | 202 | 820 | 249 |
| 0.0020 | 128 | 213 | 145 | 69 | 0.0020 | 120 | 204 | 374 | 101 |
| 0.0005 | 124 | 213 | 142 | 67 | 0.0005 | 119 | 201 | 210 | 70 |

| H-433 | | | | | H-434 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 193 | 311 | 228 | 1165 | 0.5 | 201 | 301 | 547 | 291 |
| 0.125 | 197 | 283 | 158 | 611 | 0.125 | 193 | 324 | 321 | 167 |
| 0.0313 | 196 | 278 | 170 | 268 | 0.0313 | 200 | 342 | 220 | 97 |
| 0.0078 | 171 | 320 | 189 | 124 | 0.0078 | 184 | 312 | 215 | 88 |
| 0.0020 | 145 | 327 | 222 | 91 | 0.0020 | 198 | 332 | 224 | 81 |
| 0.0005 | 224 | 301 | 193 | 80 | 0.0005 | 210 | 346 | 221 | 82 |

| H-436 | | | | | H-437 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 168 | 267 | 199 | 383 | 0.5 | 173 | 319 | 2172 | 1785 |
| 0.125 | 147 | 247 | 158 | 203 | 0.125 | 188 | 319 | 2269 | 1662 |
| 0.0313 | 154 | 284 | 188 | 131 | 0.0313 | 190 | 307 | 1819 | 1221 |
| 0.0078 | 173 | 290 | 181 | 96 | 0.0078 | 175 | 305 | 1132 | 610 |
| 0.0020 | 178 | 311 | 189 | 81 | 0.0020 | 191 | 322 | 590 | 224 |
| 0.0005 | 161 | 302 | 177 | 76 | 0.0005 | 201 | 306 | 327 | 134 |

| H-438 | | | | | H-439 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 212 | 355 | 464 | 2126 | 0.5 | 242 | 329 | 558 | 1933 |
| 0.125 | 181 | 304 | 252 | 1877 | 0.125 | 201 | 307 | 322 | 1655 |
| 0.0313 | 171 | 301 | 212 | 1174 | 0.0313 | 192 | 303 | 244 | 1092 |
| 0.0078 | 172 | 311 | 183 | 493 | 0.0078 | 183 | 294 | 209 | 485 |
| 0.0020 | 174 | 313 | 202 | 202 | 0.0020 | 188 | 289 | 198 | 194 |
| 0.0005 | 177 | 303 | 196 | 107 | 0.0005 | 196 | 307 | 215 | 116 |

TABLE 14-continued

| H-440 | | | | | H-441 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 189 | 264 | 179 | 124 | 0.5 | 189 | 632 | 2280 | 1725 |
| 0.125 | 180 | 304 | 202 | 84 | 0.125 | 183 | 303 | 1816 | 1158 |
| 0.0313 | 192 | 303 | 204 | 76 | 0.0313 | 167 | 269 | 984 | 607 |
| 0.0078 | 190 | 302 | 203 | 72 | 0.0078 | 184 | 267 | 600 | 267 |
| 0.0020 | 180 | 288 | 180 | 77 | 0.0020 | 171 | 247 | 332 | 164 |
| 0.0005 | 191 | 287 | 187 | 74 | 0.0005 | 187 | 240 | 291 | 136 |

| H-442 | | | | | H-443 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 469 | 497 | 480 | 2547 | 0.5 | 95 | 147 | 2248 | 2563 |
| 0.125 | 215 | 283 | 213 | 2311 | 0.125 | 72 | 124 | 1836 | 2178 |
| 0.0313 | 107 | 152 | 104 | 1629 | 0.0313 | 65 | 106 | 967 | 1559 |
| 0.0078 | 99 | 224 | 88 | 823 | 0.0078 | 69 | 120 | 555 | 776 |
| 0.0020 | 89 | 118 | 71 | 333 | 0.0020 | 78 | 117 | 220 | 307 |
| 0.0005 | 73 | 113 | 69 | 138 | 0.0005 | 73 | 114 | 101 | 125 |

| H-446 | | | | | H-447 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 86 | 138 | 615 | 2261 | 0.5 | 123 | 68 | 1728 | 2206 |
| 0.125 | 72 | 124 | 275 | 1974 | 0.125 | 104 | 60 | 1209 | 1529 |
| 0.0313 | 68 | 125 | 131 | 1550 | 0.0313 | 105 | 64 | 554 | 727 |
| 0.0078 | 70 | 117 | 107 | 803 | 0.0078 | 100 | 63 | 214 | 312 |
| 0.0020 | 68 | 109 | 72 | 314 | 0.0020 | 114 | 70 | 121 | 126 |
| 0.0005 | 68 | 111 | 70 | 145 | 0.0005 | 121 | 77 | 85 | 91 |

| H-448 | | | | | H-449 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 89 | 148 | 2303 | 2560 | 0.5 | 102 | 157 | 2165 | 2512 |
| 0.125 | 83 | 163 | 2044 | 2411 | 0.125 | 86 | 128 | 1781 | 2144 |
| 0.0313 | 66 | 132 | 1401 | 1864 | 0.0313 | 67 | 124 | 1029 | 1385 |
| 0.0078 | 64 | 119 | 647 | 959 | 0.0078 | 62 | 114 | 442 | 578 |
| 0.0020 | 62 | 106 | 228 | 448 | 0.0020 | 59 | 95 | 152 | 241 |
| 0.0005 | 73 | 129 | 143 | 194 | 0.0005 | 66 | 118 | 120 | 138 |

| H-451 | | | | | H-452 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 88 | 127 | 2043 | 2333 | 0.5 | 615 | 640 | 465 | 2549 |
| 0.125 | 96 | 122 | 1391 | 1625 | 0.125 | 259 | 295 | 205 | 2035 |
| 0.0313 | 76 | 116 | 597 | 689 | 0.0313 | 153 | 174 | 120 | 1156 |
| 0.0078 | 69 | 113 | 222 | 240 | 0.0078 | 115 | 144 | 89 | 485 |
| 0.0020 | 73 | 111 | 113 | 134 | 0.0020 | 107 | 143 | 83 | 166 |
| 0.0005 | 76 | 119 | 91 | 98 | 0.0005 | 89 | 144 | 88 | 163 |

| H-453 | | | | | H-454 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 284 | 264 | 2756 | 2348 | 0.5 | 139 | 129 | 3095 | 2495 |
| 0.125 | 150 | 157 | 2750 | 2036 | 0.125 | 82 | 114 | 2954 | 2577 |
| 0.0313 | 110 | 140 | 2002 | 1123 | 0.0313 | 77 | 129 | 2569 | 2272 |
| 0.0078 | 110 | 164 | 1121 | 577 | 0.0078 | 85 | 142 | 2091 | 1590 |
| 0.0020 | 96 | 173 | 388 | 215 | 0.0020 | 89 | 145 | 977 | 718 |
| 0.0005 | 84 | 156 | 165 | 104 | 0.0005 | 75 | 140 | 376 | 248 |

| H-455 | | | | | H456 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 110 | 163 | 307 | 2579 | 0.5 | 100 | 206 | 134 | 2749 |
| 0.125 | 89 | 135 | 151 | 2025 | 0.125 | 75 | 185 | 95 | 2315 |

TABLE 14-continued

| | | | | | | | | | |
|---|---|---|---|---|---|---|---|---|---|
| 0.0313 | 96 | 137 | 115 | 1482 | 0.0313 | 73 | 174 | 94 | 1555 |
| 0.0078 | 83 | 138 | 94 | 619 | 0.0078 | 77 | 171 | 75 | 683 |
| 0.0020 | 84 | 150 | 86 | 319 | 0.0020 | 92 | 152 | 86 | 234 |
| 0.0005 | 79 | 140 | 86 | 133 | 0.0005 | 87 | 153 | 87 | 106 |

| H-457 | | | | | H458 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 137 | 243 | 2873 | 2690 | 0.5 | 86 | 143 | 1268 | 2738 |
| 0.125 | 106 | 203 | 2679 | 2626 | 0.125 | 85 | 155 | 508 | 2653 |
| 0.0313 | 83 | 199 | 1971 | 2053 | 0.0313 | 87 | 151 | 207 | 2113 |
| 0.0078 | 84 | 171 | 975 | 1127 | 0.0078 | 74 | 146 | 117 | 1188 |
| 0.0020 | 67 | 201 | 328 | 497 | 0.0020 | 63 | 156 | 71 | 486 |
| 0.0005 | 89 | 213 | 201 | 199 | 0.0005 | 80 | 165 | 81 | 205 |

| H-459 | | | | | H460 | | | | |
|---|---|---|---|---|---|---|---|---|---|
| Mab (ug/ml) | BSA | HSA | CSA | FSA | Mab (ug/ml) | BSA | HSA | CSA | FSA |
| 0.5 | 95 | 150 | 2902 | 2643 | 0.5 | 88 | 155 | 2643 | 2412 |
| 0.125 | 81 | 140 | 2378 | 2158 | 0.125 | 87 | 112 | 2041 | 2012 |
| 0.0313 | 84 | 139 | 1449 | 1125 | 0.0313 | 93 | 127 | 1341 | 973 |
| 0.0078 | 86 | 147 | 605 | 442 | 0.0078 | 98 | 135 | 540 | 446 |
| 0.0020 | 78 | 147 | 239 | 174 | 0.0020 | 99 | 128 | 220 | 140 |
| 0.0005 | 87 | 143 | 123 | 96 | 0.0005 | 96 | 133 | 134 | 88 |

EXAMPLE 20

This Example compares the ability of Mabs H425 and H-352 to recognize CSA or FSA as determined using the following ELISA protocol. The wells of an ELISA plate were coated with antigen by adding to each well 100 μl of either feline serum albumin (diluted to 2 μg/ml in CBC) or canine serum albumin (CSA) (diluted to 0.5 μg/ml in CBC Buffer [50 mM carbonate/bicarbonate buffer, pH 9.6]). The plates were incubated overnight at 4° C. The following day, the wells were emptied, the plates blotted dry and 200 μl of Blocking Buffer (0.25% bovine serum albumin (BSA) in PBS) was added to each well. The plates were incubated for 30 minutes at 25° C. in an incubation chamber after which the plates were washed 4 times with Wash Buffer (0.5% Tween-20 in PBS). To each well was then added 100 μl of the indicated Mab diluted to the indicated concentration in Diluent (0.25% BSA, 5% Tween-20 in PBS). In wells serving as a blank, Diluent was added instead of an antibody. Plates were incubated at 25° C. for 2 hours after which, 100 μl of horse-radish-peroxidase (HRP)-conjugated, goat anti-mouse IgG (KPL Labs, Gaithersburg, Md.; cat. # 074-1802) (diluted 1:15,000 in Diluent) were added to each well and the plates incubated for one hour at 25° C. The plates were then washed 4 times with Wash Buffer and 100 μl of prepared TMB peroxidase substrate (KPL Labs; cat # 50-76-00) was added to each well. Plates were incubates 10 minutes at room temperature and the color reaction stopped by the addition of 100 μl of TMB Stop Solution (KPL Labs; cat # 50-76-00) to each well. Plates were read at 450 nm and the results are shown below in Table 15.

TABLE 15

| Mab conc. | CSA | | FSA | |
|---|---|---|---|---|
| (ug/ml) | H-352 | H-425 | H-352 | H-425 |
| 4.0 | 3.28 | 0.387 | | |
| 1.3 | 3.18 | 0.141 | 3.915 | 3.984 |
| 0.4 | 2.51 | 0.090 | 3.933 | 4.115 |
| 0.1 | 1.69 | 0.071 | 3.739 | 3.810 |

This Example demonstrates that Mab H-352 recognizes both CSA and FSA whereas H425 preferentially recognizes FSA as compared to CSA.

EXAMPLE 21

This Example demonstrates the effect of blood in a urine sample on the measurement of albumin in the sample.

Blood cells were diluted into a urine sample at a ratio of 1:400 and the sample serially diluted into unspiked urine. The Calculated amount of albumin in each sample was determined by calculation based on the albumin concentration in the blood sample. The Measured amount of albumin in each dilution was then measured using the ELISA assay procedure described in Example 11. The number of blood cells in each dilution was also determined by visual count (number of cells per high-powered field). In addition, the color of the sample was visually noted. The results are shown below in Table 16.

TABLE 16

| Sample Dilution | Calculated MA (mg/dl) | Measured MA (mg/dl) | Blood Dipstick | RBC/hpf | Color |
|---|---|---|---|---|---|
| 1:400 | 4.8 | 5.6 | +++ | >100 | Red |
| 1:800 | 2.4 | 2.5 | +++ | >100 | Red |
| 1:1600 | 1.2 | 1.6 | +++ | >100 | Pink |
| 1:3200 | 0.6 | 0.9 | +++ | 50-60 | Yellow |
| 1:6400 | 0.3 | 0.6 | +++ | 40-60 | Yellow |
| 1:12800 | 0.2 | 0.3 | ++ | 20-30 | Yellow |
| 1:25600 | 0.1 | 0.2 | ++ | 10-20 | Yellow |
| 0 | 0 | 0.1 | − | 0 | Yellow |

EXAMPLE 22

This Example demonstrates the relationship between age, health status and the presence of microalbuminuria (MA) in the general feline population.

Urine samples from 1243 client-owned and veterinary clinic staff-owned cats were collected by 59 veterinary clinics in 22 different states. Information submitted with each sample included age, gender, breed, urine collection method, reason for visit (well pet, neuter, dental, or medical visit), and medical history. All urine samples were tested for the presence of albumin using either the ELISA assay described in Example 11 with feline albumin (produced according to the method described in Example 17) as the coating antigen, or a dipstick-type immunoassay for feline albumin (Heska's E.R.D.—HealthScreen™ Feline Urine Test), or both the ELISA and dipstick-type assays. The anti-feline albumin antibody used in both the ELISA and the dipstick-type assay was monoclonal antibody H425.

The average age of the population tested was 7.0 years with the range being less than 1 year through 23 years. For statistical analysis, the age of each cat was rounded up to a full year and the cats were pooled into age groups of less than 3 years, 3-5 years, 6-8 years, 9-11 years, 12-15 years, and 16-23 years. The relationship between age and MA test result was evaluated using logistic regression analysis.

Table 17 shows the data for all of the cats in the study.

TABLE 17

All Cats Brought to Clinic

| Age of Cat | Total Number of Cats | Cats Positive for MA | Percent Positive for MA | Number of Cats in Pooled Group | Number of MA Positive Cats in Pooled Group | Percent MA Positive Cats in Pooled Group |
|---|---|---|---|---|---|---|
| 1 | 251 | 22 | 10.0 | | | |
| 2 | 110 | 15 | 13.6 | 361 | 40 | 11.1 |
| 3 | 83 | 15 | 18.1 | | | |
| 4 | 67 | 13 | 19.4 | | | |
| 5 | 78 | 18 | 23.1 | 228 | 46 | 20.2 |
| 6 | 55 | 18 | 32.7 | | | |
| 7 | 65 | 12 | 18.5 | | | |
| 8 | 64 | 11 | 17.2 | 184 | 41 | 22.3 |
| 9 | 62 | 16 | 25.8 | | | |
| 10 | 65 | 17 | 26.2 | | | |
| 11 | 53 | 12 | 22.6 | 180 | 45 | 25.0 |
| 12 | 52 | 17 | 32.7 | | | |
| 13 | 58 | 25 | 43.1 | | | |
| 14 | 50 | 20 | 40.0 | | | |
| 15 | 53 | 21 | 39.6 | 213 | 83 | 39.0 |
| 16 | 32 | 20 | 62.5 | | | |
| 17 | 21 | 14 | 66.7 | | | |
| 18 | 13 | 8 | 61.5 | | | |
| 19 | 5 | 2 | 40.0 | | | |
| 20 | 3 | 3 | 100 | | | |
| 21 | 2 | 2 | 100 | | | |
| 22 | | | | | | |
| 23 | 1 | 1 | 100 | 77 | 50 | 64.9 |
| | 1243 | 305 | 24.5 | 1243 | 305 | 24.5 |

The data in Table 17 show a statistically significant correlation (P<0.0001) between increasing age and a positive microalbuminuria test. The relationship between age and a positive microalbuminuria test is defined by a logarithmic function with both prevalence and incidence increasing with age. The rapid increase in prevalence in older cats is analogous to other geriatric conditions in which incidence of disease increases with age.

Of the 1243 cats examined in the study, 610 were characterized as visiting the veterinarian for a spay, neuter, or well pet check with no medical history listed. The average age of this population was 4.8 years. Table 18 shows the microalbuminuria data for cats in this cohort.

TABLE 18

Cats Brought to Clinic as Well-Pets

| Age of Cat | Total Number of Cats | Cats Positive for MA | Percent Positive for MA | Number of Cats in Pooled Group | Number of MA Positive Cats in Pooled Group | Percent MA Positive Cats in Pooled Group |
|---|---|---|---|---|---|---|
| 1 | 218 | 16 | 7.3 | | | |
| 2 | 69 | 7 | 10.1 | 287 | 23 | 8.0 |
| 3 | 44 | 4 | 9.1 | | | |
| 4 | 32 | 6 | 18.8 | | | |
| 5 | 36 | 3 | 8.3 | 112 | 13 | 11.6 |
| 6 | 24 | 4 | 16.7 | | | |
| 7 | 32 | 2 | 6.3 | | | |

TABLE 18-continued

Cats Brought to Clinic as Well-Pets

| Age of Cat | Total Number of Cats | Cats Positive for MA | Percent Positive for MA | Number of Cats in Pooled Group | Number of MA Positive Cats in Pooled Group | Percent MA Positive Cats in Pooled Group |
|---|---|---|---|---|---|---|
| 8 | 27 | 4 | 14.8 | 83 | 10 | 12.0 |
| 9 | 22 | 6 | 27.3 | | | |
| 10 | 19 | 2 | 10.5 | | | |
| 11 | 17 | 1 | 5.9 | 58 | 9 | 15.5 |
| 12 | 17 | 4 | 23.5 | | | |
| 13 | 19 | 10 | 52.6 | | | |
| 14 | 11 | 3 | 27.3 | | | |
| 15 | 12 | 4 | 33.3 | 59 | 21 | 35.6 |
| 16 | 5 | 5 | 100 | | | |
| 17 | 2 | 1 | 50.0 | | | |
| 18 | | | | | | |
| 19 | 3 | 1 | 33.3 | | | |
| 20 | | | | | | |
| 21 | | | | | | |
| 22 | | | | | | |
| 23 | 1 | 1 | 100 | 11 | 8 | 72.7 |
| | 610 | 84 | 13.8 | 610 | 84 | 13.8 |

Analysis of the data in Table 18 revealed a statistically significant correlation between increasing age and a positive microalbuminuria test result in apparently healthy cats.

Of the 1243 cats in the study, 345 were characterized as visiting the veterinarian for a medical reason (excluding elective procedures such as dental prophylaxis, spay, neuter, declaw) and a specific medical history was listed. Medical conditions consisted of those routinely seen by practicing veterinarians such as dental disease, feline lower urinary tract disease (FLUTD), inflammatory bowel disease (IBD), diabetes, hyperthyroidism, vomiting, upper respiratory infection, renal disease, and neoplasia. The average age of this population was 9.5 years. Table 19 shows the microalbuminuria data for cats in this cohort.

TABLE 19

Cats Brought to Clinic for Medical Reason

| Age of Cat | Total Number of Cats | Cats Positive for MA | Percent Positive for MA | Number of Cats in Pooled Group | Number of MA Positive Cats in Pooled Group | Percent MA Positive Cats in Pooled Group |
|---|---|---|---|---|---|---|
| 1 | 9 | 4 | 44.4 | | | |
| 2 | 22 | 5 | 22.7 | 31 | 9 | 29.0 |
| 3 | 22 | 11 | 50.0 | | | |
| 4 | 21 | 6 | 28.6 | | | |
| 5 | 21 | 11 | 52.4 | 64 | 28 | 43.8 |
| 6 | 17 | 11 | 64.7 | | | |
| 7 | 16 | 7 | 43.8 | | | |
| 8 | 18 | 6 | 33.3 | 51 | 24 | 47.1 |
| 9 | 19 | 5 | 26.3 | | | |
| 10 | 25 | 10 | 40.0 | | | |
| 11 | 23 | 8 | 34.8 | 67 | 23 | 34.3 |
| 12 | 15 | 4 | 26.7 | | | |
| 13 | 25 | 10 | 40.0 | | | |
| 14 | 19 | 8 | 42.1 | | | |
| 15 | 27 | 12 | 44.4 | 86 | 34 | 39.5 |
| 16 | 22 | 13 | 59.1 | | | |
| 17 | 12 | 9 | 75.0 | | | |
| 18 | 10 | 6 | 60.0 | | | |
| 19 | | | | | | |
| 20 | 1 | 1 | 100 | | | |
| 21 | 1 | 1 | 100 | | | |
| 22 | | | | | | |
| 23 | | | | 46 | 30 | 65.2 |
| | 345 | 148 | 42.9 | 345 | 148 | 42.9 |

Although the invention has been described with reference to the presently preferred embodiments, it should be understood to those skilled in the art that various modifications can be made without departing from the spirit of the invention. Accordingly, the invention is limited only by the following claims.

What is claimed is:

1. An isolated monoclonal antibody that selectively binds albumin from a fetid or a canid, wherein said antibody binds the same epitope recognized by the monoclonal antibody produced by the hybridoma cell line having ATCC Accession No. PTA-9498 (MAb H425).

2. A kit comprising:

(a) an isolated monoclonal antibody that selectively binds albumin from a feud or canid, wherein said antibody binds the same epitope recognized by the monoclonal antibody produced by the hybridoma cell line having ATCC Accession No. PTA-9498 (MAb H425); and (b) a means for detecting the amount of albumin in a sample collected from a felid or canid, wherein said means detects albumin in a range from about 10 μg/ml to about 50 μg/ml.

* * * * *

UNITED STATES PATENT AND TRADEMARK OFFICE

CERTIFICATE OF CORRECTION

PATENT NO. : 7,482,128 B2
APPLICATION NO. : 10/550563
DATED : January 27, 2009
INVENTOR(S) : Wayne A. Jensen et al.

It is certified that error appears in the above-identified patent and that said Letters Patent is hereby corrected as shown below:

Column 43, line 9, Claim 1 please replace “fetid” with --felid--.
Column 44, line 3, Claim 2 please replace “feud” with --felid--.

Signed and Sealed this

Twenty-third Day of June, 2009

John Doll

JOHN DOLL
*Acting Director of the United States Patent and Trademark Office*